US010271949B2

(12) United States Patent
Dakin et al.

(10) Patent No.: US 10,271,949 B2
(45) Date of Patent: Apr. 30, 2019

(54) PARAVALVULAR LEAK OCCLUSION DEVICE FOR SELF-EXPANDING HEART VALVES

(71) Applicant: St. Jude Medical, Cardiology Division, Inc., St. Paul, MN (US)

(72) Inventors: Gregory James Dakin, Minneapolis, MN (US); Peter Nicholas Braido, Wyoming, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 94 days.

(21) Appl. No.: 14/096,427

(22) Filed: Dec. 4, 2013

(65) Prior Publication Data

US 2014/0277426 A1 Sep. 18, 2014

Related U.S. Application Data

(63) Continuation-in-part of application No. 13/797,513, filed on Mar. 12, 2013.

(51) Int. Cl.
*A61B 17/08* (2006.01)
*A61F 2/24* (2006.01)

(52) U.S. Cl.
CPC ............ *A61F 2/246* (2013.01); *A61F 2/2418* (2013.01); *A61F 2/24* (2013.01); *A61F 2/2412* (2013.01);
(Continued)

(58) Field of Classification Search
CPC ........ A61B 17/12022; A61B 17/12136; A61B 17/12172; A61B 17/12113; A61B 17/12118; A61F 2/24; A61F 2/2409; A61F 2/2412; A61F 2/2418; A61F 2/2427; A61F 2/243; A61F 2/2433; A61F 2/2436; A61F 2/2439; A61F 2/2451; A61F 2/246; A61F 2/2466; A61F 2250/0003; A61F 2250/0069; A61F 2/07; A61F 2002/077; A61F 2002/823; A61F 2/2415; A61F 2/2421;
(Continued)

(56) References Cited

U.S. PATENT DOCUMENTS 3,571,815 A * 3/1971 Somyk .................. A61F 2/2424
623/2.4
3,657,744 A 4/1972 Ersek
(Continued)

FOREIGN PATENT DOCUMENTS

DE 19857887 A1 7/2000
DE 10121210 A1 11/2002
(Continued)

OTHER PUBLICATIONS

Kit Definition, Collins English Dictionary.*
(Continued)

*Primary Examiner* — Elizabeth Houston
*Assistant Examiner* — Kankindi Rwego
(74) *Attorney, Agent, or Firm* — Lerner, David, Littenberg, Krumholz & Mentlik, LLP

(57) ABSTRACT

An occluder device for occluding a gap between a medical device and adjacent body tissue includes a conformable body having a hollow interior, a leading end and a trailing end; and a port disposed at the trailing end of the body and in fluid communication with the interior of the body.

13 Claims, 20 Drawing Sheets

(52) U.S. Cl.
CPC ............... *A61F 2250/0003* (2013.01); *A61F 2250/0069* (2013.01)

(58) Field of Classification Search
CPC .... A61F 2/2424; A61F 2/2463; A61F 2/2469; A61F 2/2472; A61F 2/2475; A61F 2/2496; A61F 2250/006; A61F 2250/0062; A61F 2250/0063; A61F 2/954; A61F 2/958; A61F 2/962; A61F 2/966; A61F 2/97; A61F 2002/9505; A61F 2002/9511; A61F 2002/9517; A61F 2002/9522; A61F 2002/9528; A61F 2002/9534; A61F 2002/9583; A61F 2002/9586; A61F 2002/9665; A61M 2025/1052; A61M 2025/1054; A61M 2025/1086

See application file for complete search history.

(56) References Cited

U.S. PATENT DOCUMENTS

| | | |
|---|---|---|
| 4,275,469 A | 6/1981 | Gabbay |
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,420,016 A * | 5/1995 | Boguslaski ............ C12Q 1/04 106/2 |
| 5,474,563 A * | 12/1995 | Myler ................ A61F 2/91 606/108 |
| 5,480,423 A | 1/1996 | Ravenscroft et al. |
| 5,613,950 A * | 3/1997 | Yoon ............ A61B 17/00234 600/225 |
| 5,843,167 A | 12/1998 | Dwyer et al. |
| 5,846,261 A | 12/1998 | Kotula et al. |
| 5,855,601 A | 1/1999 | Bessler et al. |
| 5,935,163 A | 8/1999 | Gabbay |
| 5,961,549 A | 10/1999 | Nguyen et al. |
| 6,041,785 A * | 3/2000 | Webb ............ A61B 17/12022 128/887 |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 6,951,573 B1 | 10/2005 | Dilling |
| 6,986,786 B1 | 1/2006 | Smith |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz et al. |
| 7,247,167 B2 | 7/2007 | Gabbay |
| 7,267,686 B2 | 9/2007 | DiMatteo et al. |
| 7,276,078 B2 * | 10/2007 | Spenser ............ A61F 2/2409 623/1.24 |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,573 B2 | 5/2008 | Gabbay |
| 7,381,218 B2 | 6/2008 | Schreck |
| 7,381,219 B2 | 6/2008 | Salahieh et al. |
| 7,452,371 B2 | 11/2008 | Pavcnik et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,892,281 B2 | 2/2011 | Seguin et al. |
| 7,914,569 B2 | 3/2011 | Nguyen et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 7,981,153 B2 * | 7/2011 | Fogarty ............ A61B 17/0401 623/1.26 |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |

(56) References Cited

U.S. PATENT DOCUMENTS

| | | |
|---|---|---|
| 8,449,599 B2 | 5/2013 | Chau et al. |
| 8,449,604 B2 | 5/2013 | Moaddeb et al. |
| 8,454,686 B2 | 6/2013 | Alkhatib |
| 8,500,798 B2 | 8/2013 | Rowe et al. |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,685,080 B2 | 4/2014 | White |
| 8,728,154 B2 | 5/2014 | Alkhatib |
| 8,747,459 B2 | 6/2014 | Nguyen et al. |
| 8,764,820 B2 | 7/2014 | Dehdashtian et al. |
| 8,795,357 B2 | 8/2014 | Yohanan et al. |
| 8,801,776 B2 | 8/2014 | House et al. |
| 8,808,356 B2 | 8/2014 | Braido et al. |
| 8,828,078 B2 | 9/2014 | Salahieh et al. |
| 8,834,563 B2 | 9/2014 | Righini |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |
| 8,974,523 B2 | 3/2015 | Thill et al. |
| 8,974,524 B2 | 3/2015 | Yeung et al. |
| 9,339,274 B2 | 5/2016 | Dakin |
| 2002/0036220 A1 | 3/2002 | Gabbay |
| 2003/0023303 A1 | 1/2003 | Palmaz et al. |
| 2003/0028209 A1* | 2/2003 | Teoh ................ A61B 17/12022 606/191 |
| 2003/0050694 A1 | 3/2003 | Yang et al. |
| 2003/0130726 A1 | 7/2003 | Thorpe et al. |
| 2003/0181942 A1 | 9/2003 | Sutton et al. |
| 2004/0044391 A1 | 3/2004 | Porter |
| 2004/0049262 A1 | 3/2004 | Obermiller et al. |
| 2004/0093075 A1 | 5/2004 | Kuehne |
| 2004/0111111 A1 | 6/2004 | Lin |
| 2004/0143288 A1* | 7/2004 | Searle ............... A61B 17/12022 606/200 |
| 2004/0210304 A1 | 10/2004 | Seguin et al. |
| 2004/0260389 A1 | 12/2004 | Case et al. |
| 2005/0096726 A1 | 5/2005 | Sequin et al. |
| 2005/0137682 A1 | 6/2005 | Justino |
| 2005/0137695 A1 | 6/2005 | Salahieh et al. |
| 2005/0137697 A1 | 6/2005 | Salahieh et al. |
| 2005/0203605 A1 | 9/2005 | Dolan |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0161249 A1 | 7/2006 | Realyvasquez et al. |
| 2006/0173532 A1 | 8/2006 | Flagle et al. |
| 2006/0178740 A1 | 8/2006 | Stacchino et al. |
| 2006/0195181 A1* | 8/2006 | Johnson ................ A61F 2/2412 623/2.11 |
| 2006/0206199 A1* | 9/2006 | Churchwell ..... A61B 17/12022 623/1.25 |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2006/0287717 A1* | 12/2006 | Rowe .................. A61F 2/2412 623/2.11 |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0050008 A1* | 3/2007 | Kim ................. A61B 17/12022 623/1.13 |
| 2007/0050012 A1 | 3/2007 | Densford |
| 2007/0055355 A1 | 3/2007 | Kim et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0162048 A1 | 7/2007 | Quinn et al. |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0265656 A1 | 11/2007 | Amplatz et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0099653 A1 | 4/2009 | Suri et al. |
| 2009/0112309 A1 | 4/2009 | Jaramillo et al. |
| 2009/0112311 A1* | 4/2009 | Miles .................. A61F 2/24 623/2.38 |
| 2009/0138079 A1 | 5/2009 | Tuval et al. |
| 2009/0276027 A1 | 11/2009 | Glynn |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0082094 A1* | 4/2010 | Quadri .................. A61F 2/2412 623/1.26 |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0066233 A1* | 3/2011 | Thornton ......... A61B 17/00234 623/2.11 |
| 2011/0098800 A1 | 4/2011 | Braido et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0264206 A1 | 10/2011 | Tabor |
| 2012/0035722 A1 | 2/2012 | Tuval |
| 2012/0078347 A1 | 3/2012 | Braido et al. |
| 2012/0078358 A1* | 3/2012 | Vidlund .......... A61B 17/00234 623/2.36 |
| 2012/0101572 A1 | 4/2012 | Kovalsky et al. |
| 2012/0123529 A1 | 5/2012 | Levi et al. |
| 2012/0303116 A1 | 11/2012 | Gorman, III et al. |

(56) References Cited

U.S. PATENT DOCUMENTS

| | | | | |
|---|---|---|---|---|
| 2013/0197622 | A1* | 8/2013 | Mitra | A61F 2/07 623/1.15 |
| 2013/0274873 | A1 | 10/2013 | Delaloye et al. | |
| 2014/0121763 | A1 | 5/2014 | Duffy et al. | |
| 2014/0155997 | A1 | 6/2014 | Braido | |
| 2014/0214159 | A1 | 7/2014 | Vidlund et al. | |
| 2014/0228946 | A1 | 8/2014 | Chau et al. | |
| 2014/0303719 | A1 | 10/2014 | Cox et al. | |
| 2014/0324164 | A1 | 10/2014 | Gross et al. | |
| 2014/0343671 | A1 | 11/2014 | Yohanan et al. | |
| 2014/0350668 | A1 | 11/2014 | Delaloye et al. | |
| 2014/0350669 | A1 | 11/2014 | Gillespie et al. | |

FOREIGN PATENT DOCUMENTS

| | | | |
|---|---|---|---|
| DE | 202008009610 U1 | 12/2008 | |
| EP | 0850607 A1 | 7/1998 | |
| EP | 1000590 A1 | 5/2000 | |
| EP | 1360942 A1 | 11/2003 | |
| EP | 1584306 A1 | 10/2005 | |
| EP | 1598031 A2 | 11/2005 | |
| EP | 2537487 A1 | 12/2012 | |
| FR | 2847800 A1 | 6/2004 | |
| FR | 2850008 A1 | 7/2004 | |
| WO | 9117720 A1 | 11/1991 | |
| WO | 9716133 A1 | 5/1997 | |
| WO | 9832412 A2 | 7/1998 | |
| WO | 9913801 A1 | 3/1999 | |
| WO | 0128459 A1 | 4/2001 | |
| WO | 0149213 A2 | 7/2001 | |
| WO | 0154625 A1 | 8/2001 | |
| WO | 0156500 A2 | 8/2001 | |
| WO | 0176510 A2 | 10/2001 | |
| WO | 0236048 A1 | 5/2002 | |
| WO | 0247575 A2 | 6/2002 | |
| WO | 03047468 A1 | 6/2003 | |
| WO | 2006073626 A2 | 7/2006 | |
| WO | 2007071436 A2 | 6/2007 | |
| WO | 2008070797 A2 | 6/2008 | |
| WO | 2010008548 A2 | 1/2010 | |
| WO | 2010008549 A1 | 1/2010 | |
| WO | 2010096176 A1 | 8/2010 | |
| WO | 2010098857 A1 | 9/2010 | |
| WO | WO2013037519 | * | 3/2013 |

OTHER PUBLICATIONS

"Cuff." YourDictionary,n.d. Web. Feb. 26, 2016.<http://www.yourdictionary.com/cuff>.*
Catheter-implanted prosthetic heart valves, Knudsen, L.L., et al., The International Journal of Artificial Organs, vol. 16, No. 5 1993, pp. 253-262.
Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
Quaden et al., "Percutaneous aortic valve replacement: resection before implantation", pp. 836-840, European J. of Cardio-thoracic Surgery, 27 (2005).
Ruiz, Carlos, Overview of PRE-CE Mark Transcatheter Aortic Valve Technologies, Euro PCR, dated May 25, 2010.
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.
U.S. Appl. No. 29/375,243, filed Sep. 20, 2010.
U.S. Appl. No. 29/375,260, filed Sep. 20, 2010.
78. Heart repairs without surgery. Minimally invasive procedures aim to correct valve leakage. PubMed ID 15586429.
Buellesfeld et al., Treatment of paravalvular leaks through inverventional techniques; Department of Cardiology, Ben University Hospital 2011.
De Cicco, Giuseppe, et al. "Aortic valve periprosthetic leakage: anatomic observations and surgical results." The Annals of thoracic surgery 79.5 (2005): 1480-1485.
Gössl, Mario, and Charanjit S. Rihal. "Percutaneous treatment of aortic and mitral valve paravalvular regurgitation." Current cardiology reports 15.8 (2013): 1-8.
Muñoz, Daniel Rodriguez, Carla Lázaro Rivera, and José Luis Zamorano Gómez. "Guidance of treatment of perivalvular prosthetic leaks." Current cardiology reports 16.1 (2014): 1-6.
Rohde, I., Masch, J.-M., Theisen-Kunde, D., Marczynski-Bühlow, M., Bombien Quaden, R., Lutter, G. and Brinkmann, R. (2015), Resection of Calcified Aortic Heart Leaflets In Vitro by Q-Switched 2?μm Microsecond Laser Radiation. Journal of Cardiac Surgery, 30: 157-162. doi: 10.1111/jocs.12481.
Swiatkiewicz, Iwona, et al. "Percutaneous closure of mitral perivalvular leak." Kardiologia polska 67.7 (2009): 762.
Transcatheter Umbrella Closure of Valvular and Paravalvular Leaks, Hourihan et al., Journal of the American College of Cardiology, vol. 20, No. 6, pp. 1371-1377, (1992).

* cited by examiner

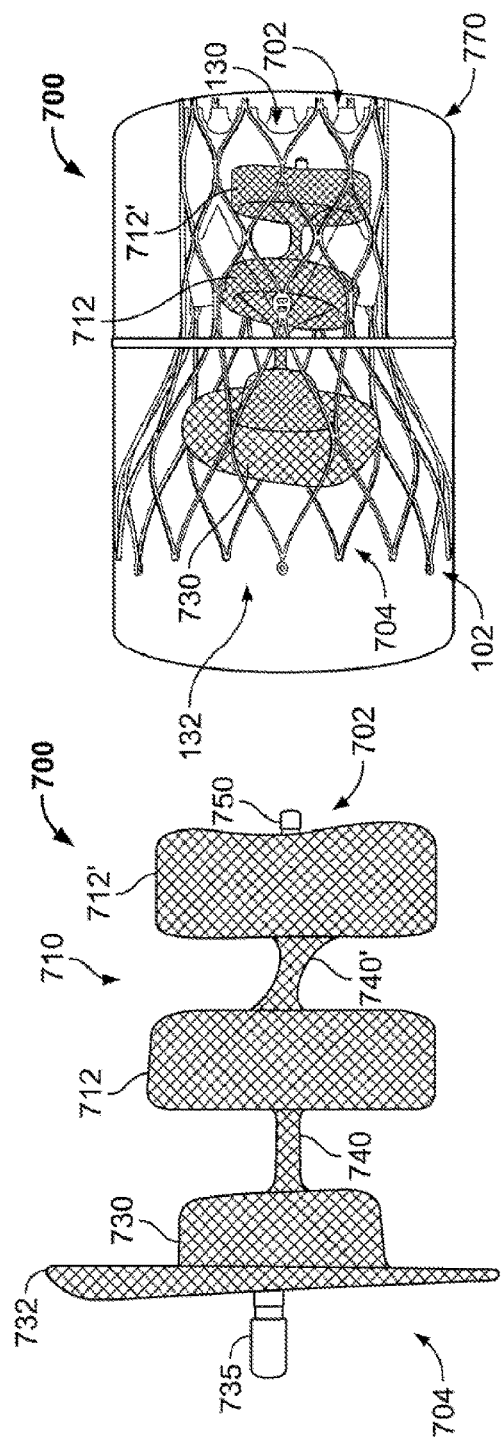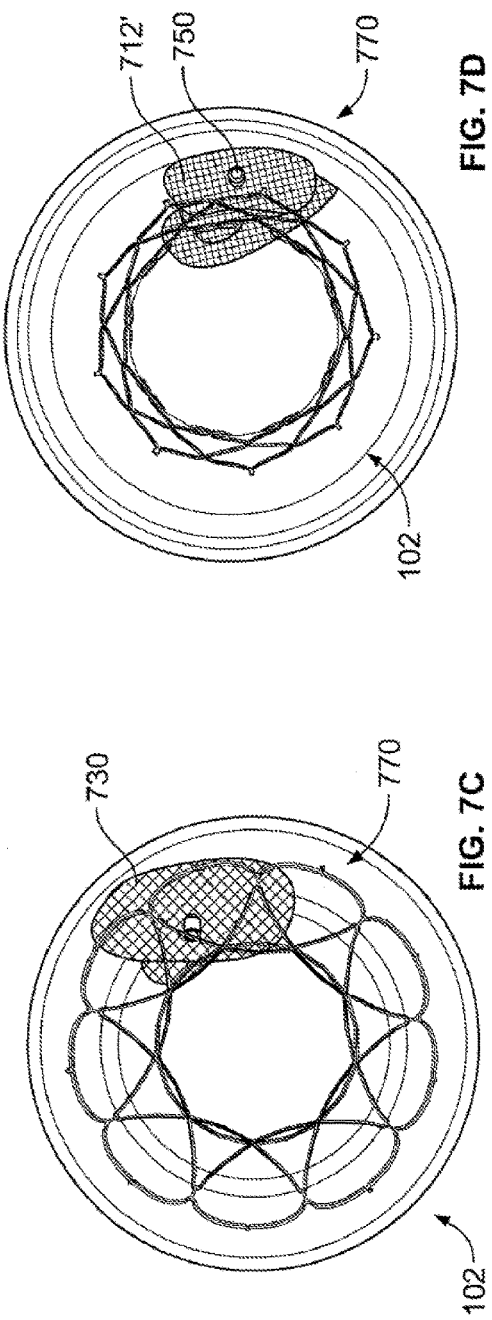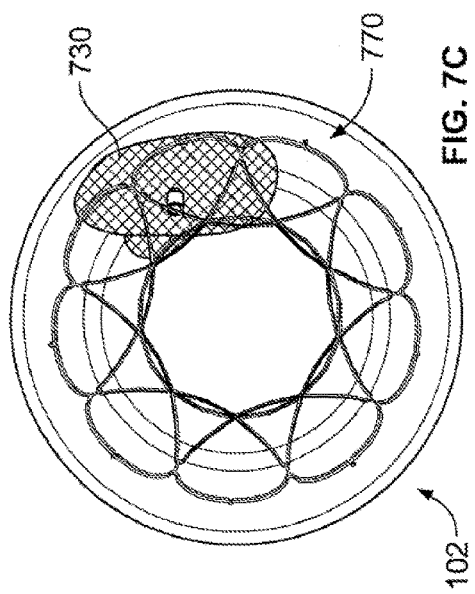

PARAVALVULAR LEAK OCCLUSION DEVICE FOR SELF-EXPANDING HEART VALVES

CROSS-REFERENCES TO RELATED APPLICATIONS

The present application is a continuation-in-part of U.S. patent application Ser. No. 13/797,513, filed Mar. 12, 2013, the disclosure of which is hereby incorporated herein by reference.

BACKGROUND OF THE INVENTION

The present disclosure relates in general to heart valve replacement and, in particular, to collapsible prosthetic heart valves. More particularly, the present disclosure relates to devices and methods for positioning and sealing of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent or a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

SUMMARY OF THE INVENTION

In some embodiments, an occluder device for occluding a gap between a medical device and adjacent body tissue includes an expandable body having a first end and a second end, a fastener coupled to the first end of the body, and an expandable disk coupled to the second end of the body.

In some embodiments, a method for occluding a gap between a prosthetic heart valve and adjacent body tissue includes delivering an occluder into the interior of the heart valve, the occluder having (i) an expandable body, (ii) a fastener coupled to one end of the body, and (iii) an expandable disk coupled to another end of the body. The occluder is advanced through a cell of the heart valve to the outside of the heart valve. The fastener is coupled to one end of the prosthetic heart valve and the expandable disk is coupled to the prosthetic heart valve at a position spaced from the one end.

BRIEF DESCRIPTION OF THE DRAWINGS

Various embodiments of the present disclosure are described herein with reference to the drawings, wherein:

FIG. 7A is a side view of a conformable occluder in accordance with another embodiment of the present disclosure;

FIGS. 7B-D are side, top and bottom views showing the use of the conformable occluder of FIG. 7A in vitro;

DETAILED DESCRIPTION

Figure 1:
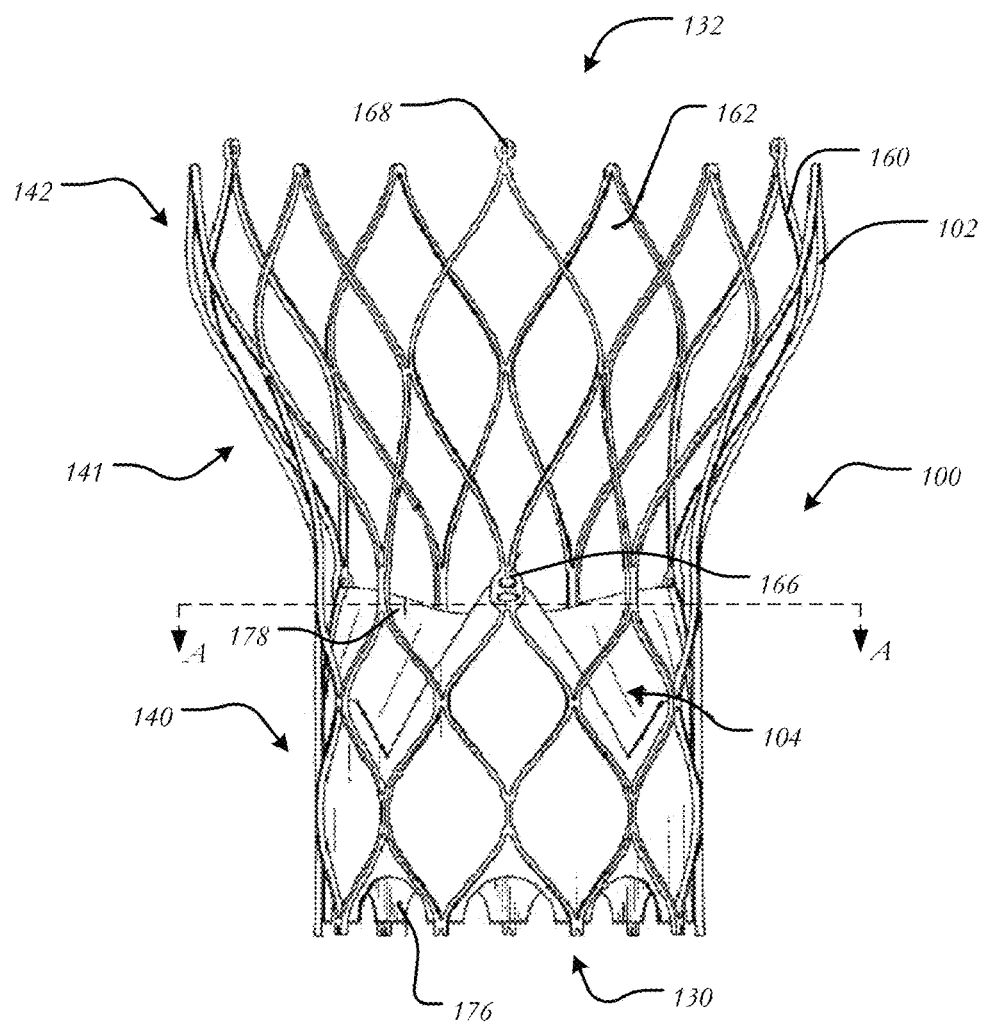
FIG. 1 is a side elevational view of a conventional prosthetic heart valve.

Despite the various improvements that have been made to the collapsible prosthetic heart valve delivery process, conventional devices suffer from some shortcomings. For example, with conventional self expanding valves, clinical success of the valve is dependent on accurate deployment and anchoring. Inaccurate deployment and anchoring of the valve increases risks, such as those associated with valve migration, which may cause severe complications and possibly death due to the obstruction of the left ventricular outflow tract. Inaccurate deployment and anchoring may also result in the leakage of blood between the implanted heart valve and the native valve annulus, commonly referred to as paravalvular (otherwise known as perivalvular) leakage. This leakage enables blood flow from the aorta back into the left ventricle, reducing cardiac efficiency and putting a greater strain on the heart muscle. Additionally, calcification of the aortic valve may affect performance and the interaction between the implanted valve and the calcified tissue is believed to be relevant to leakage, as will be outlined below.

Moreover, anatomical variations between patients may require removal of a fully deployed heart valve from the patient if it appears that the valve is not functioning properly. Removing a fully deployed heart valve increases the length of the procedure and increases the risk of infection and/or damage to heart tissue. Thus, methods and devices are desirable that would reduce the likelihood of removal. Methods and devices are also desirable that would reduce the likelihood of paravalvular leakage through gaps formed between the implanted heart valve and patient tissue.

There therefore is a need for further improvements to the devices, systems, and methods for transcatheter delivery and positioning of collapsible prosthetic heart valves. Specifically, there is a need for further improvements to the devices, systems, and methods for accurately implanting a prosthetic heart valve. Among other advantages, the present disclosure may address one or more of these needs.

Various embodiments of the present invention will now be described with reference to the appended drawings. It is to be appreciated that these drawings depict only some embodiments of the invention and are therefore not to be considered limiting of its scope.

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used in connection with devices for delivering a prosthetic heart valve or other medical device into a patient, the terms "trailing" and "leading" are to be taken as relative to the user of the delivery devices. "Trailing" is to be understood as relatively close to the user, and "leading" is to be understood as relatively farther away from the user. Also as used herein, the terms "about," "generally" and "substantially" are intended to mean that slight deviations from absolute are included within the scope of the term so modified.

The leak occluders of the present invention may be used in connection with collapsible prosthetic heart valves. FIG. 1 shows one such collapsible stent-supported prosthetic heart valve 100 including a stent 102 and a valve assembly 104 as known in the art. The prosthetic heart valve 100 is designed to replace a native tricuspid valve of a patient, such as a native aortic valve. It should be noted that while the inventions herein are described predominately in connection with their use with a prosthetic aortic valve and a stent having a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

Prosthetic heart valve 100 will be described in more detail with reference to FIG. 1. Prosthetic heart valve 100 includes expandable stent 102 which may be formed from, for example, a shape memory material, such as the nickel-titanium alloy known as "Nitinol" or other suitable metals, and in particular, from those materials that are capable of self-expansion. Stent 102 extends from proximal or annulus end 130 to a distal or aortic end 132, and includes annulus section 140 adjacent proximal end 130, transition section 141 and aortic section 142 adjacent distal end 132. Annulus section 140 has a relatively small cross-section in the expanded condition, while aortic section 142 has a relatively large cross-section in the expanded condition. Preferably, annulus section 140 is in the form of a cylinder having a substantially constant diameter along its length. Transition section 141 may taper outwardly from annulus section 140 to aortic section 142. Each of the sections of stent 102 includes a plurality of struts 160 forming cells 162 connected to one another in one or more annular rows around the stent. For example, as shown in FIG. 1, annulus section 140 may have two annular rows of complete cells 162 and aortic section 142 and transition section 141 may each have one or more annular rows of partial cells 162. Cells 162 in aortic section 142 may be larger than cells 162 in annulus section 140. The larger cells in aortic section 142 better enable prosthetic valve 100 to be positioned in the native valve annulus without the stent structure interfering with blood flow to the coronary arteries.

Stent 102 may also include a plurality of commissure features 166 for attaching the commissure between two adjacent leaflets to stent 102. As can be seen in FIG. 1, commissure features 166 may lie at the intersection of four cells 162, two of the cells being adjacent one another in the same annular row, and the other two cells being in different annular rows and lying in end-to-end relationship. Preferably, commissure features 166 are positioned entirely within annulus section 140 or at the juncture of annulus section 140 and transition section 141. Commissure features 166 may include one or more eyelets which facilitate the suturing of the leaflet commissure to the stent.

Stent 102 may include one or more retaining elements 168 at distal end 132 thereof, retaining elements 168 being sized and shaped to cooperate with female retaining structures (not shown) provided on the deployment device. The engagement of retaining elements 168 with the female retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed.

Prosthetic heart valve 100 includes valve assembly 104 preferably positioned in annulus section 140 of the stent 102 and secured to the stent. Valve assembly 104 includes cuff 176 and a plurality of leaflets 178 which collectively function as a one-way valve by coapting with one another. As a prosthetic aortic valve, valve 100 has three leaflets 178, as well as three commissure features 166. However, it will be appreciated that other prosthetic heart valves with which the leak occluders of the present invention may be used may have a greater or lesser number of leaflets 178 and commissure features 166.

Although cuff 176 is shown in FIG. 1 as being disposed on the luminal or inner surface of annulus section 140, it is contemplated that cuff 176 may be disposed on the abluminal or outer surface of annulus section 140 or may cover all or part of either or both of the luminal and abluminal surfaces. Both cuff 176 and leaflets 178 may be wholly or partly formed of any suitable biological material or polymer such as, for example, polytetrafluoroethylene (PTFE), ultra-high molecular weight polyethylene (UHMWPE), silicone, or polyethylene terephthalate (PET) or combinations thereof.

Prosthetic heart valve 100 may be used to replace a native aortic valve, a surgical heart valve or a heart valve that has undergone a surgical procedure. The prosthetic heart valve may be delivered to the desired site (e.g., near the native aortic annulus) using any suitable delivery device. During delivery, prosthetic heart valve 100 is disposed inside the delivery device in the collapsed condition. The delivery device may be introduced into a patient using a transfemoral, transapical, transseptal or any other percutaneous approach. Once the delivery device has reached the target site, the user may deploy prosthetic heart valve 100. Upon deployment, prosthetic heart valve 100 expands so that annulus section 140 is in secure engagement within the native aortic annulus. When prosthetic heart valve 100 is properly positioned inside the heart, it works as a one-way valve, allowing blood to flow from the left ventricle of the heart to the aorta, and preventing blood from flowing in the opposite direction.

Problems may be encountered when implanting prosthetic heart valve 100. For example, in certain procedures, collapsible valves may be implanted in a native valve annulus without first resecting the native valve leaflets. The collapsible valves may have critical clinical issues because of the nature of the stenotic leaflets that are left in place. Additionally, patients with uneven calcification, bi-cuspid aortic valve disease, and/or valve insufficiency cannot be treated well, if at all, with the current collapsible valve designs. Similar issues may be encountered due to undersizing, improper placement or seating of a heart valve or off-axis placement within the patient anatomy.

The reliance on unevenly calcified leaflets for proper valve placement and seating could lead to several problems, such as paravalvular leakage (PV leak), which can have severe adverse clinical outcomes. To reduce these adverse events, the optimal valve would anchor adequately and seal without the need for excessive radial force that could harm nearby anatomy and physiology.

Figure 2:
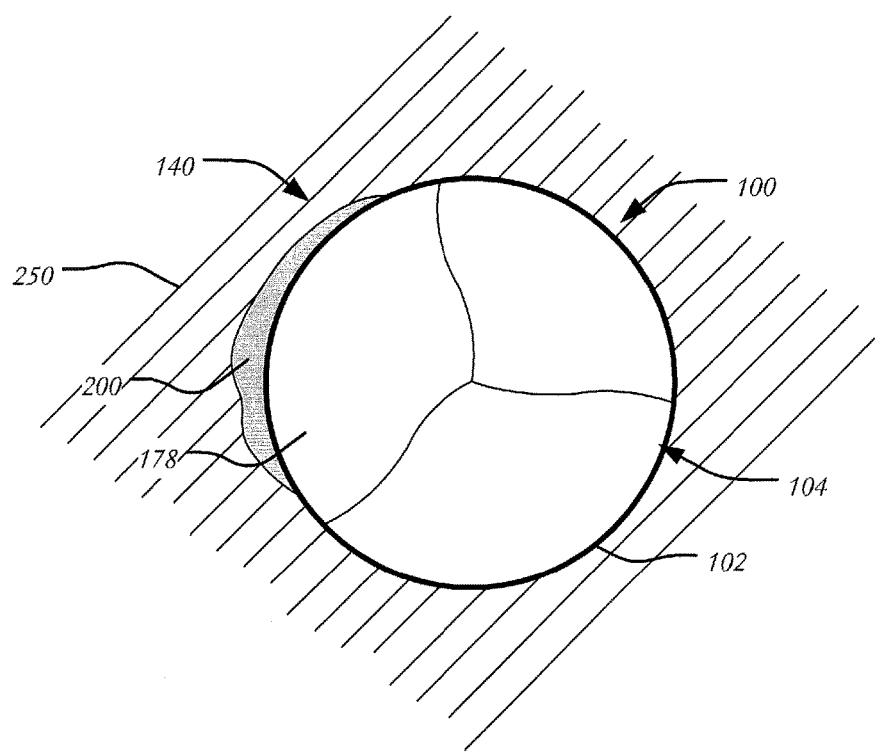
FIG. 2 is a highly schematic cross-sectional view taken along line A-A of FIG. 1 and showing the prosthetic heart valve disposed within a native valve annulus.

FIG. 2 is a highly schematic cross-sectional illustration of prosthetic heart valve 100 disposed within native valve annulus 250. As seen in the figure, annulus section 140 of the stent 102 has a substantially circular cross-section which is disposed within the non-circular native valve annulus 250. At certain locations around the perimeter of heart valve 100, crescent-shaped gaps 200 form between heart valve 100 and native valve annulus 250. Blood flowing through these gaps and past valve assembly 104 of prosthetic heart valve 100 can cause regurgitation and other inefficiencies which reduce cardiac performance. Such improper fitment may be due to suboptimal native valve annulus geometry due, for example, to calcification of native valve annulus 250 or to unresected native leaflets.

Figure 3A:
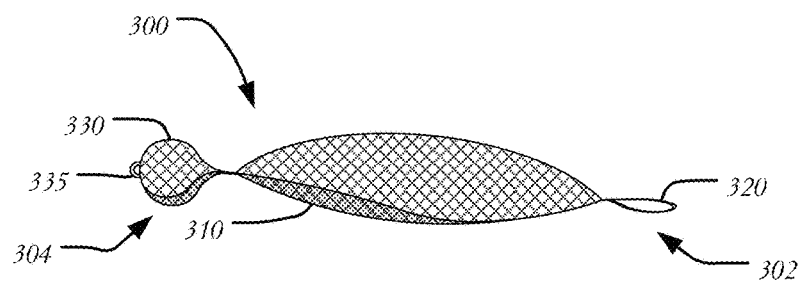
FIG. 3A is a side view of a conformable occluder in accordance with one embodiment of the present disclosure.
Figure 3B:
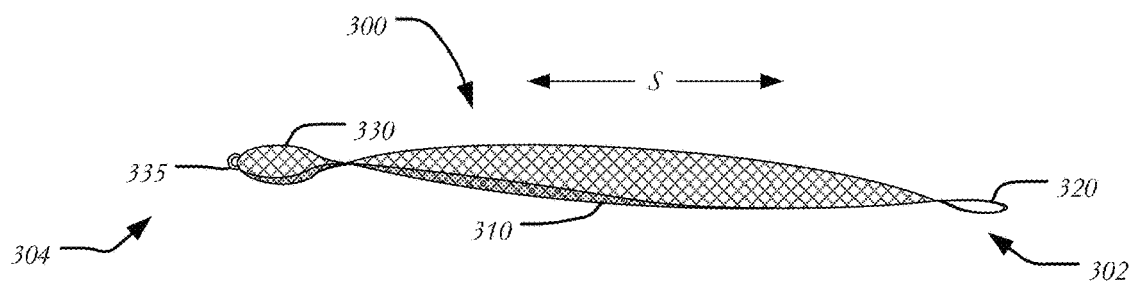
FIG. 3B is a side view of the conformable occluder of FIG. 3A after it has been stretched longitudinally.

FIGS. 3A and 3B illustrate one embodiment of conformable occluder 300 intended to fill irregularities between heart valve 100 and native valve annulus 250 shown in FIG. 2. As will be described in more detail below, conformable occluder 300 allows for superior sealing between the perimeter of heart valve 100 and native valve annulus 250 while affording a low radial outward force. FIG. 3A shows conformable occluder 300 in a relaxed and expanded configuration, while FIG. 3B shows conformable occluder 300 in a stretched and partially elongated configuration. Conformable occluder 300 has a leading end 302 and a trailing end 304, and may generally include body 310, fastener 320, and disk 330.

Body 310 may be a metallic structure that may be longitudinally stretched in the direction of arrows S from the relaxed condition shown in FIG. 3A to the stretched condition shown in FIG. 3B. In the relaxed condition, body 310 may have a cross-section that is greater in size than it is in the stretched condition. Thus, body 310 of conformable occluder 300 may be flexible and capable of contracting in the radial direction when a force is applied thereto to conform to the shape of the annulus in which it will be implanted. Moreover, the ability of body 310 to longitudinally stretch in the direction of arrows S will enable the occluder to be delivered through a small diameter catheter and to be secured between two attachment points as will be seen below with reference to FIGS. 4A-4F.

Occluder 300 may be formed from a tubular section of braided fabric comprising a plurality of braided strands. The strands forming the braid may have a predetermined relative orientation with respect to one another (e.g., a helical braid). The ends of the strands may be located at leading end 302 and trailing end 304, and maybe affixed to one another to prevent unraveling by any suitable means such as soldering, brazing, welding, gluing, tying, or clamping. Moreover, occluder 300 may comprise a plurality of layers of braided fabric and/or other occluding material (e.g., see filler 345 in FIG. 3C) such that occluder 300 is capable of at least partially inhibiting blood flow therethrough in order to facilitate the formation of thrombus and epithelialization.

Occluder 300 may be formed, for example, of a shape-memory material, of a super-elastic material, of a biocompatible polymer, or of another material that is capable of collapsing and expanding. In the embodiments depicted in FIGS. 3A-3C, occluder 300 comprises a braided metal fabric that is both resilient and capable of heat treatment to substantially set a desired preset shape (e.g., the relaxed configuration shown in FIG. 3A). One class of materials which meets these qualifications is shape memory alloys. One example of a shape memory alloy is Nitinol. It is also understood that occluder 300 may comprise various materials other than Nitinol that have elastic and/or memory properties, such as spring stainless steel, trade named alloys such as Elgiloy® and Hastelloy®, CoCrNi alloys (e.g., trade name Phynox), MP35N®, CoCrMo alloys, a mixture of metal and polymer fibers or a braided fabric. Occluder 300 may further include a coating such as polymer sheets, tissue or collagen. Depending on the individual material selected, strand diameter, number of strands, and pitch may be altered to achieve the desired properties of occluder 300.

As further described below, body 310 may be collapsed during delivery into the patient and re-expanded after delivery to occlude gaps between a prosthetic heart valve and the native valve annulus to one side of the valve. While body 310 is shown in FIG. 3A as having an elliptical longitudinal cross-section in the expanded condition, it will be understood that the body may be constructed with various shapes and/or sizes. For example, body 310 may have a circular, oval, polygonal, square, diamond, triangular or other shape in longitudinal cross-section when expanded. Body 310 may also include two or more segments. Additionally, body 310 may be formed of multiple layers of braid to decrease occlusion time.

Body 310 may be connected to fastener 320 at leading end 302 of conformable occluder 300. Fastener 320 may be formed of a suture, polymeric fiber, metallic filament, such as a flexible stranded stainless steel cable or loop of nitinol wire, or other suitable material, and may be configured to secure conformable occluder 300 to prosthetic heart valve 100 as will be described in greater detail below. Though fastener 320 is shown in FIG. 3A as a loop, it will be understood that a simple hook, clasp or other similar structure capable of grasping, clipping, or hooking conformable occluder 300 to a strut 160 of prosthetic heart valve 100 may be used.

Body 310 may further be coupled to disk 330 at trailing end 304 of conformable occluder 300. In the depicted embodiment, body 310 is coupled to disk 330 by a small diameter waist. Disk 330 may be an ovular or spherical body sized to couple conformable occluder 300 to a cell of a prosthetic heart valve. Specifically, disk 330 may be sized larger than a cell 162 of stent 102 such that it is incapable of passing through the cell (see FIG. 1). Disk 330 may be formed of the same material as body 310 or from a different material. For example, disk 330 may be formed of a braided nitinol mesh or other shape-memory mesh. It is also contemplated that disk 330 may be constructed from a biocompatible polymer material. Disk 330 may include a lip (not shown) having a greater cross-sectional dimension than disk 330. Female component 335 connected to disk 330 at trailing end 304 may be used to couple conformable occluder 300 to a delivery device to position and deliver conformable occluder 300. Female component 335 may include an internally threaded screw attachment, a ring, or any other suitable means for coupling with a delivery device.

Figure 3C:
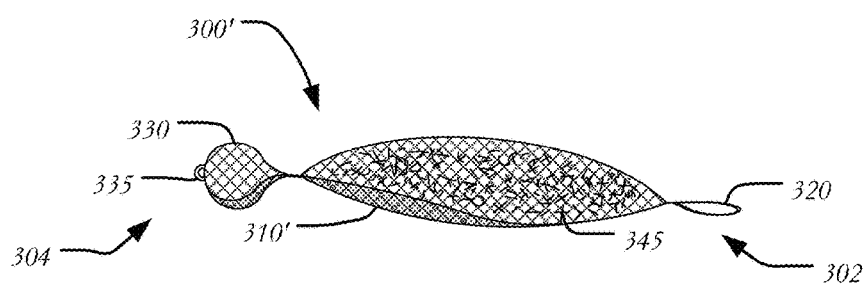
FIG. 3C is a side view of a conformable occluder having a filler in accordance with another embodiment of the present invention.

In one example, as shown in FIG. 3C, body 310' may be hollow and may be at least partially filled with filler 345 of a fabric or fibers of materials that are intertwined within the mesh of conformable occluder 300' to assist with sealing, occlusion and healing. For example, body 310' may include filler 345 of polyester threads or polyester fabric, as well as any suitable fiber material to increase density and/or promote tissue growth. Filler 345 may also be in the form of a foam material, such as a closed cell sponge. The density of body 310' may be such that it impedes the flow of blood through it. Inclusion of filler 345 in body 310' may speed occlusion time for conformable occluder 300'.

Figure 3D:
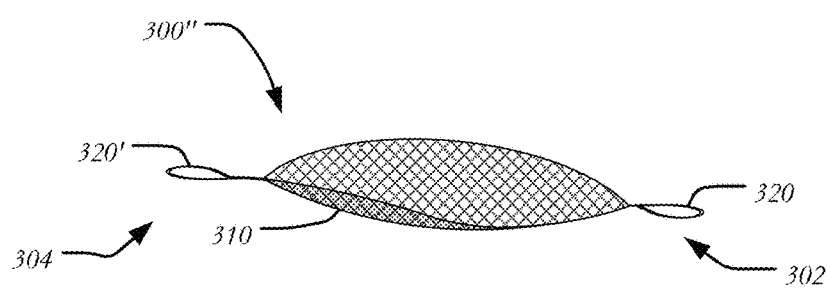
FIG. 3D is a side view of a conformable occluder having two fasteners in accordance with another embodiment of the present invention.

In an alternative embodiment, shown in FIG. 3D, occluder 300" has leading end 302 and trailing end 304, and may generally include body 310 extending from leading end 302 to trailing end 304. As seen in FIG. 3D, occluder 300" includes first fastener 320 at leading end 302. Instead of a disk on the opposite end (see disk 330 in FIGS. 3A-3C), occluder 300" includes second fastener 320' disposed near trialing end 304. In this embodiment, occluder 300" may be coupled to select struts 160 of stent 102 via first and second fasteners 320,320' without the need for disk 330.

Figure 4A:
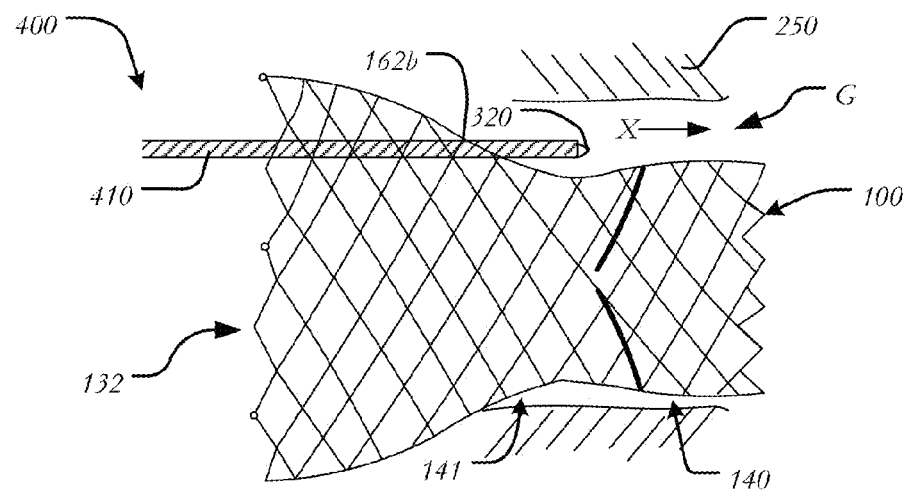
FIGS. 4A-F illustrate the steps used to insert a conformable occluder to seal a prosthetic heart valve within a native valve annulus.

FIGS. 4A-F illustrate the steps used to insert conformable occluder 300 (or conformable occluder 300' or conformable occluder 300") to seal heart valve 100 within native valve annulus 250. As seen in FIG. 4A, heart valve 100 has been implanted in a patient with annulus portion 140 thereof positioned in native valve annulus 250. Gap G may be formed between heart valve 100 and native valve annulus 250 to one side of heart valve 100.

Figure 4B:
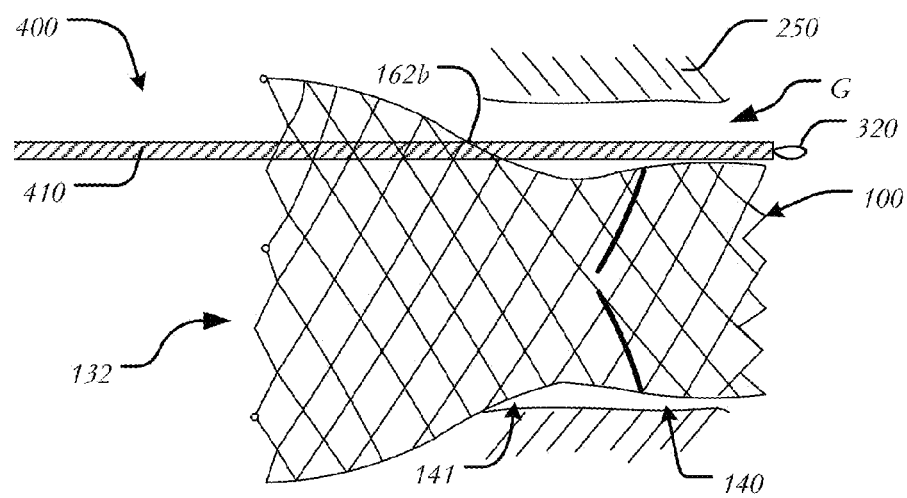

As an initial step to seal gap G, conformable occluder 300 may be disposed within delivery system 400 (FIG. 4A) in a collapsed condition, such as the stretched or elongated configuration shown in FIG. 3B. Delivery system 400 may include outer sheath 410 and inner wire 420 having male component 425. Male component 425 may include a conventional screw attachment, a terminal hook or other suitable structure for mating with female component 335. Male component 425 is configured to couple with female component 335 of conformable occluder 300 (elements shown uncoupled in FIG. 4F). Outer sheath 410 is slidable relative to inner wire 420. Delivery system 400 may be inserted into the patient and advanced toward the implanted heart valve 100 in the direction of arrow X. As it reaches heart valve 100, delivery system 400 may be advanced into the heart valve 100 at aortic end 132 and out therefrom through cell 162b in transition section 141 (shown in FIG. 4A). Delivery system 400 may then be further advanced through gap G toward annulus end 140 of implanted heart valve 100, as shown in FIG. 4B. If heart valve 100 or delivery system 400 includes echogenic materials, such materials may be used to guide delivery system 400 to the appropriate position using the assistance of three-dimensional echocaradiography to visualize heart valve 100 within the patient.

Figure 4C:
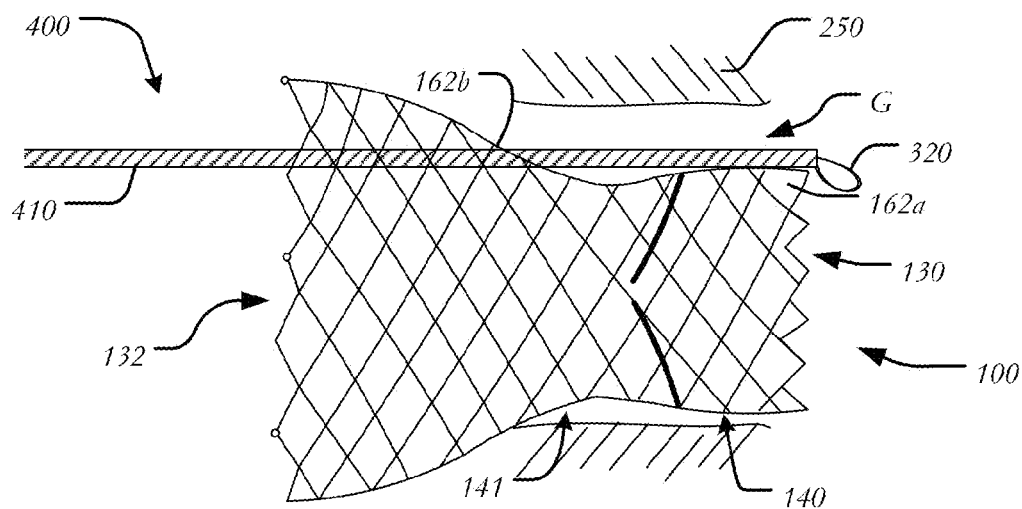
Figure 4D:
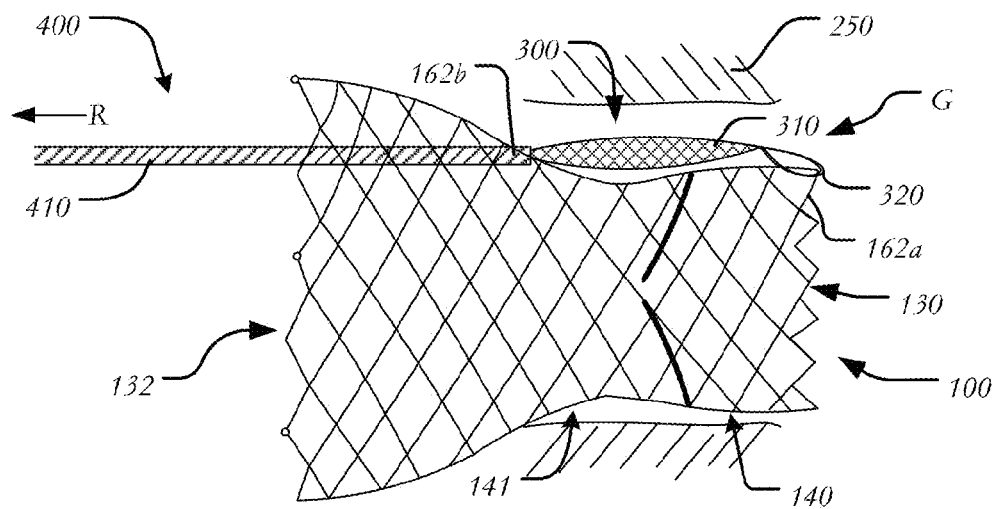

Once delivery system 400 has reached the desired site of sealing (e.g., gap G) as shown in FIG. 4C, outer sheath 410 may be retracted slightly in the direction of arrow R (toward the trailing end of delivery system 400) to expose fastener 320 and a portion of body 310 (shown in FIG. 4D). Conformable occluder 300 remains coupled to inner wire 420 at this stage and trailing edge 304 of occluder 300 remains housed within delivery system 400.

Figure 4E:
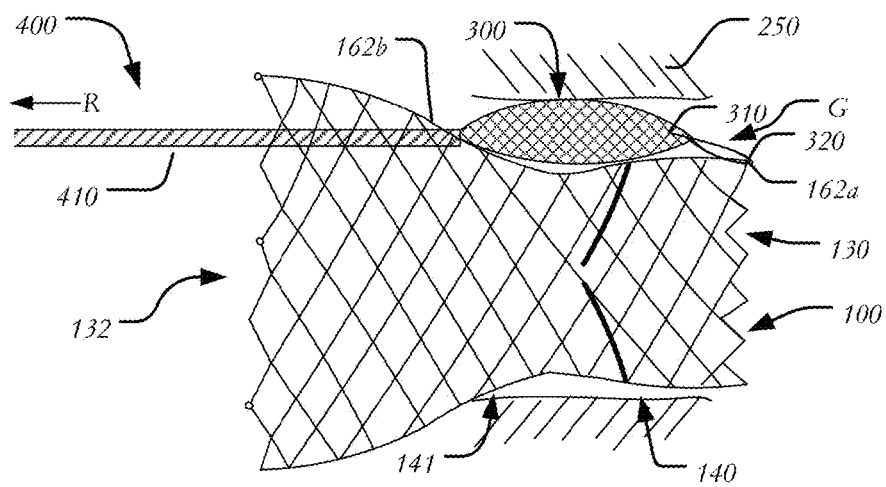
Figure 4F:
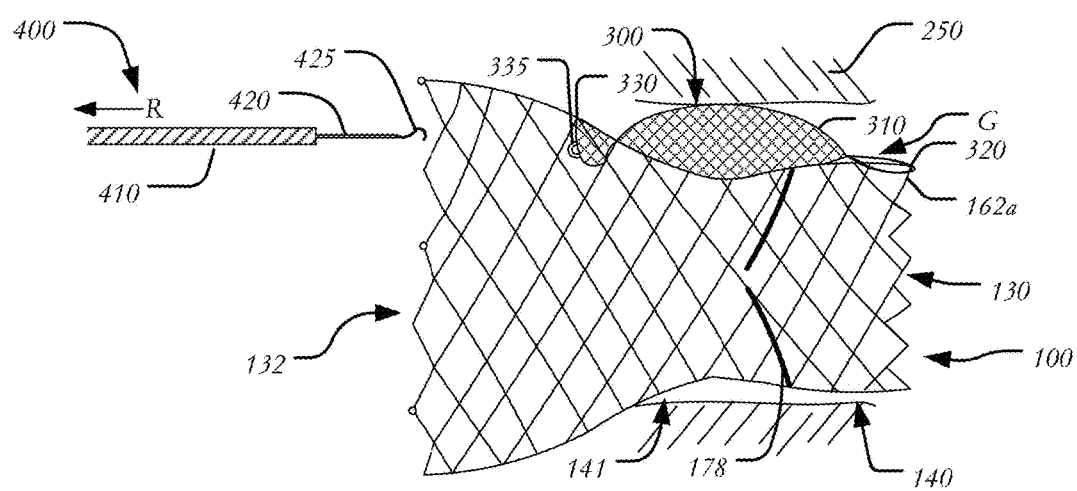

Delivery system 400 may be manipulated by gently twisting and/or tilting delivery system 400 to position fastener 320 over the apex of cell 162a at annulus end 130 of heart valve 100. Once fastener 320 has latched onto or been looped around the apex of cell 162a, outer sheath 410 may be further retracted in the direction of arrow R to expose body 310 of conformable occluder 300. As outer sheath 410 is further retracted, more of occluder body 310 is exposed and occluder 300 expands within the gap G between heart valve 100 and native valve annulus 250 (FIGS. 4D and 4E). As seen in FIGS. 4D-4F, body 310 is positioned parallel to annulus section 140 and transition section 141. In this intermediate stage of deployment, body 310 has expanded to its relaxed state and contacted the walls of native valve annulus 250, and substantially fills gap G.

Outer sheath 410 may then be fully retracted to expose disk 330 and allow it to expand near cell 162b. In the depicted embodiment, disk 330 is located on the interior of heart valve 100, although in other embodiments, disk 330 is located on the exterior of heart valve 100. In either instance, disk 330 is spaced away from valve assembly 104 so as not to impede the normal function of leaflets 178. Disk 330 then expands to a size small enough to project partially out of or into cell 162b, but remains too large to pass through that cell. The interference of disk 330 with cell 162b creates a second attachment region for conformable occluder 300. Thus, conformable occluder 300 is stretched between the two attachment regions, the interference between disk 330 and cell 162b and the connection between fastener 320 and cell 162a. Fastener 320 prevents occluder 300 from migrating into the aorta, while disc 330 prevents occluder 300 from migrating back into the heart. Alternatively, in embodiments having two fasteners instead of disk 330, such as that shown in FIG. 3D, first fastener 320 may be coupled to the apex of cell 162a, while second fastener 320' may be likewise coupled over the apex of a cell at aortic end 132 of stent 100.

Male component 425 may be disconnected from female component 335 by manipulating (e.g., rotating) wire 420. Alternatively, inner wire 420 may comprise a suture tied to female component 335, and the suture may be simply cut to release conformable occluder 300 from delivery system 400. In another example, the male and female components may be threaded and delivery system 400 may be twisted relative to occluder 300 to decouple the two from one another. Accordingly, many mating solutions between delivery system 400 and occluder 300 would serve the intended purpose for deployment of occluder 300. FIG. 4F illustrates heart valve 100 in its fully expanded state with conformable occluder 300 fully filling the gap G between heart valve 100 and native valve annulus 250. Delivery system 400 may then be withdrawn in the direction of arrow R and removed from the patient, leaving conformable occluder 300 in place to seal valve 100 within native valve annulus 250.

Figure 5:
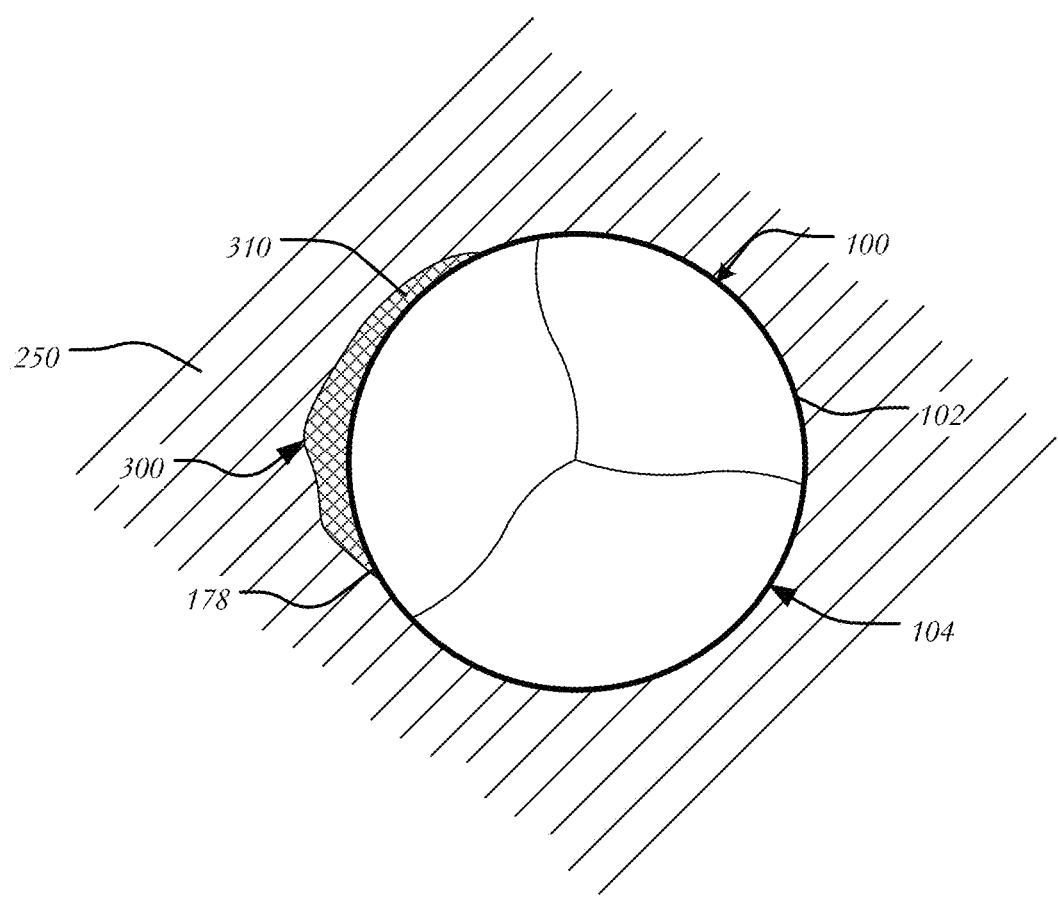
FIG. 5 is a highly schematic cross-sectional view showing a prosthetic heart valve disposed within a native valve annulus along with a conformable occluder in its fully expanded state.

FIG. 5 is a highly schematic cross-sectional view showing conformable occluder 300 in its relaxed state with body 310 fully radially expanded to fill crescent-shaped gap 200 shown in FIG. 2. The mesh of conformable occluder 300 may be capable of promoting tissue growth between heart valve 100 and native valve annulus 250. For example, conformable occluder 300 may be treated with a biological or chemical agent to promote tissue growth on the conformable occluder, further sealing the heart valve within the native valve annulus. Alternatively, conformable occluder 300 may be sufficiently dense through the use of polyester fibers or polyester fabric to adequately seal the heart valve without the need for major tissue growth throughout gap G. Occluder 300 may also be double-layered and/or may include tighter braiding to more quickly occlude the space between heart valve 100 and native valve annulus 250. When conformable occluder 300 is functioning properly, heart valve 100 will be adequately sealed within native valve annulus 250 so that blood flows through valve assembly 104 and leaflets 178, while limiting or at least reducing blood flow through any gaps formed between heart valve 100 and native valve annulus 250.

Figure 6A:
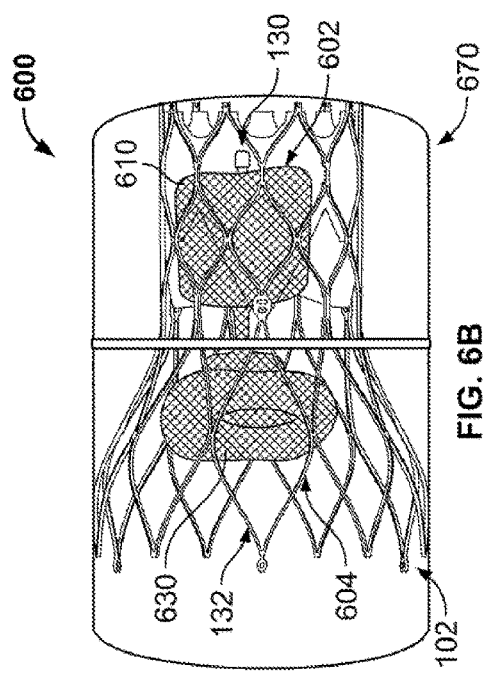
FIG. 6A is a side view of a conformable occluder in accordance with another embodiment of the present disclosure.

FIG. 6A illustrates another embodiment of conformable occluder 600. Conformable occluder 600 extends between leading end 602 and trailing end 604, and may generally include a tubular body 610 and disk 630. Disk 630 includes an enlarged outer rim 632 and is coupled to connector 635 for mating with a delivery system (not shown). As seen in FIG. 6A, reduced diameter neck portion 640 connects body 610 to disk 630. A fastener (not shown) may be attached to joint 650 at leading end 602 to connect occluder 600 to the apex of a cell 162 as described above with reference to FIGS. 4A-4F.

Figure 6B:
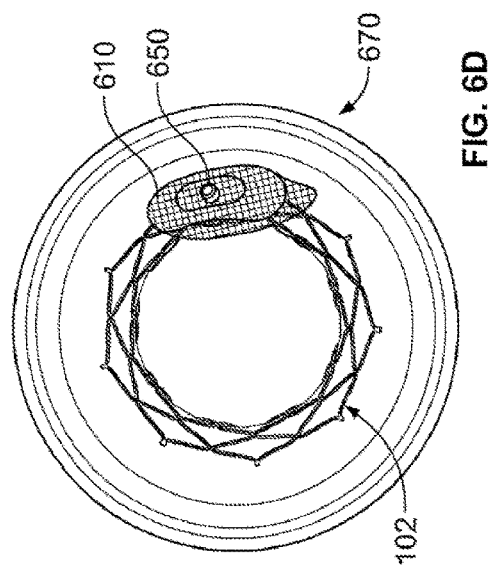
FIGS. 6B-D are side, top and bottom views showing the use of the conformable occluder of FIG. 6A in vitro.
Figure 6C:
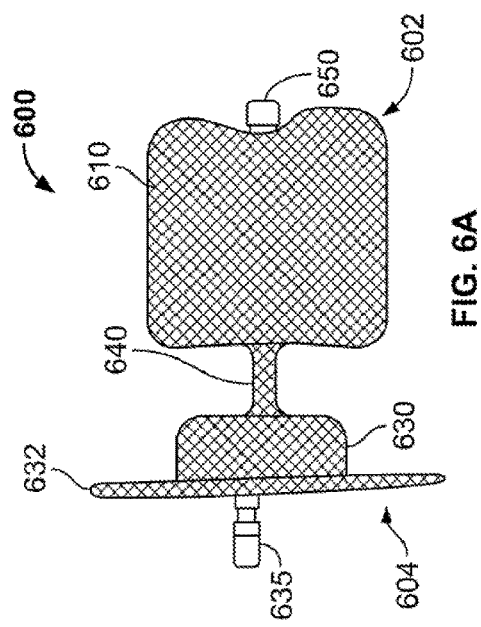
Figure 6D:
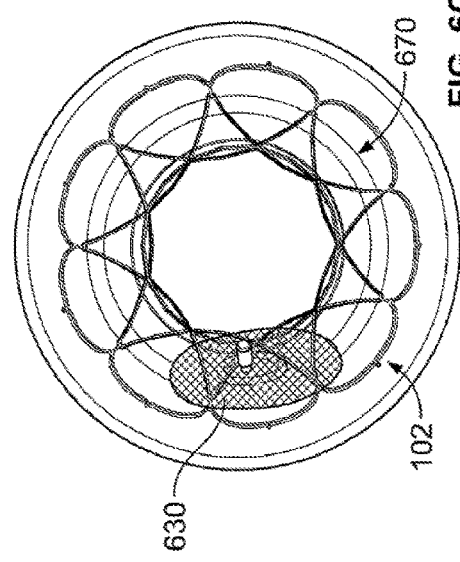

FIGS. 6B-D are a side view, and top and bottom end views illustrating the use of occluder 600. Specifically, FIG. 6B shows a side view of the system, while FIG. 6C illustrates a top view (e.g., as seen from aortic end 132 of stent 102) and FIG. 6D illustrates a bottom view (e.g., as seen from annulus end 130 of stent 102). In these figures, container 670 approximates the native valve annulus and stent 102 is disposed therein to simulate a prosthetic heart valve 100. A valve assembly is not shown attached to stent 102 for the sake of clarity. As seen in FIGS. 6B-D, occluder 600 is coupled to stent 102 and shown to fill a gap between stent 102 and the native valve annulus, approximated by the walls of container 670. Specifically, disk 630 is shown disposed within the interior of stent 102 (FIG. 6C) and body 610 is disposed outside of stent 102 (FIG. 6D). Though a fastener is not shown, it will be understood that a fastener may attach to joint 650 and couple leading end 602 of occluder 600 to the apex of a cell at annulus end 130 of stent 102. Occluder 600 may be delivered and positioned in a manner similar to that described above with reference to FIGS. 4A-F.

FIG. 7A illustrates another embodiment of conformable occluder 700. Conformable occluder 700 extends between leading end 702 and trailing end 704, and may generally include a body 710 formed of two body segments 712,712', and disk 730. Though occluder 700 is shown having two segments 712,712', it will be understood that three or more segments may be employed in constructing occluder 700. In some instances, it may be helpful to use multiple segments 712,712' as opposed to a single unitary body to improve occlusion. For example, first segment 712 may expand to a small radius, while second segment 712' may expand to a larger radius to accommodate a non-uniform native valve annulus and fill multiple gaps at varying longitudinal extents.

Disk 730 includes an enlarged outer rim 732 and is coupled to connector 735 for mating with a delivery system (not shown). As seen in FIG. 7A, two reduced diameter neck portions 740,740' connect disk 730 to first segment 712, and first segment 712 to second segment 712', respectively. A fastener (not shown) may be attached to joint 750 at leading end 702 to connect occluder 700 to the apex of a cell 162 as described above with reference to FIGS. 4A-4F.

FIGS. 7B-D are a side view, and top and bottom end views illustrating the use of occluder 700 within a container 770 approximating the native valve annulus as described above with reference to FIGS. 6B-6D. As seen in FIGS. 7B-D, occluder 700 is coupled to stent 102 and shown to fill a gap between stent 102 and the native valve annulus, approximated by the walls of container 770. It will be understood that the patient anatomy is rarely perfectly cylindrical and that occluder 700 may contour to crescent or serpentine cavities. Specifically, disk 730 is shown disposed within the interior of stent 102 (FIG. 6C) and segments 712,712' are disposed outside of stent 102 (FIG. 6D). Though a fastener is not shown, it will be understood that a fastener may attach to joint 750 to couple leading end 702 of occluder 700 to the apex of a cell at annulus end 130 of stent 102. Occluder 700 may be delivered and positioned in a manner similar to that described above with reference to FIGS. 4A-F.

FIGS. 8A-D illustrate several additional embodiments of conformable occluders 800 intended to fill irregularities between a heart valve and a native valve annulus. Occluders 800 may include any of the features of the aforementioned embodiments and be formed of like materials. In one embodiment shown in FIG. 8A, conformable occluder 800A has a leading end 802A and a trailing end 804A, and may generally include an elongated balloon-like body 810A extending between leading end 802A and trailing end 804A.

Body 810A may be a metallic structure as described above. Alternatively, body 810A may be formed of any suitable flexible material having in-growth properties, such as shape memory foams or fabrics including polyester and polyethylene terephthalate (PETE), commonly referred to by the brand name DACRON®. Such materials may be impregnated with collagen to improve sealing. Biocompatible or biodegradable materials may also be used to form body 810A such patient tissue or polymers such as polyvinyl alcohol (PVA), urethane, silicone and combinations of same or cellulose-based material, which do not have an adverse effect on the prosthetic and/or the native anatomy.

Body 810A may be formed of a compressible material that is collapsed for easier delivery into the patient and re-expanded after delivery to occlude gaps between a prosthetic heart valve and the native valve annulus to one side of the valve. Body 810A may be hollow and balloon-like, and may further include one or more ports 820A in communication with the interior of body 810A for filling body 810A with a filler F, as will be described in greater detail below with reference to FIG. 10. For ease of filling, port 820A may be disposed near trailing end 804A.

Figure 8A:
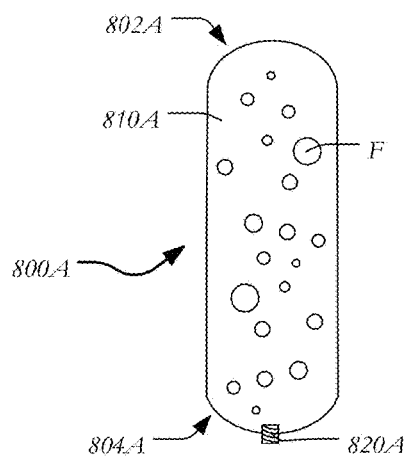
FIGS. 8A-D are side views of several additional embodiments of a conformable occluder.
Figure 8B:
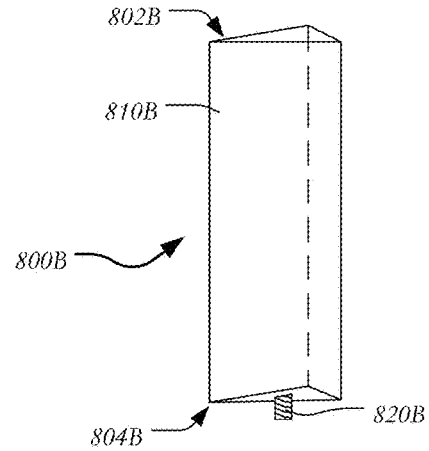
Figure 8C:
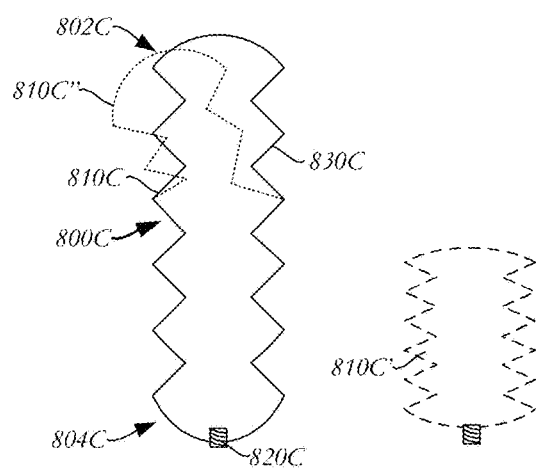
Figure 8D:
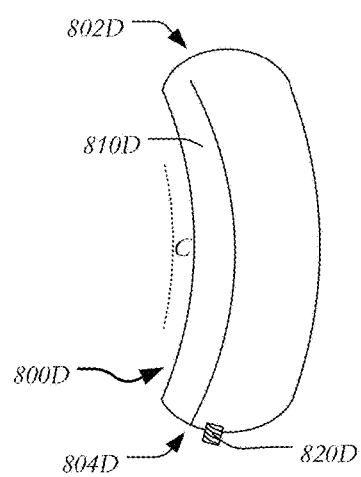

In a variation shown in FIG. 8B, occluder 800B includes leading end 802B, trailing end 804B and body 810B extending between leading end 802B and trailing end 804B. Body 810B may include a filling port 820B near trailing end 804B. Body 810B may be formed of material similar to that of body 810A but may be shaped as a triangular prism.

In a third variation (FIG. 8C), occluder 800C includes leading end 802C, trailing end 804C and body 810C extending between leading end 802C and trailing end 804C. Body 810C may include a filling port 820C near trailing end 804C. Body 810C may be accordion-like and include a number of bellows 830C which fold such that body 810C axially collapses on itself to form body 810C'. Moreover, when bellows 830C are unevenly spaced at two sides of the body, body 810C may be bent as illustrated by bent body 810C" to move and comply with the patient's anatomy for better sealing. In this example, body 810C may be formed of any of the materials discussed above and may also be formed of expandable coils (e.g., platinum coils).

In yet another variation (FIG. 8D), occluder 800D extends between leading end 802D and trailing end 804D and includes body 810D having filling port 820D near trailing end 804D. Body 810D is substantially crescent-shaped and includes a curvature C that complements the curvature of an adjacent heart valve. Moreover, in some variations of the embodiments of FIGS. 8A-D, body 810 may be formed of a shape-memory material that returns to a predetermined shape (e.g., tubular, accordion-like, crescent, etc.) after delivery.

Figure 9:
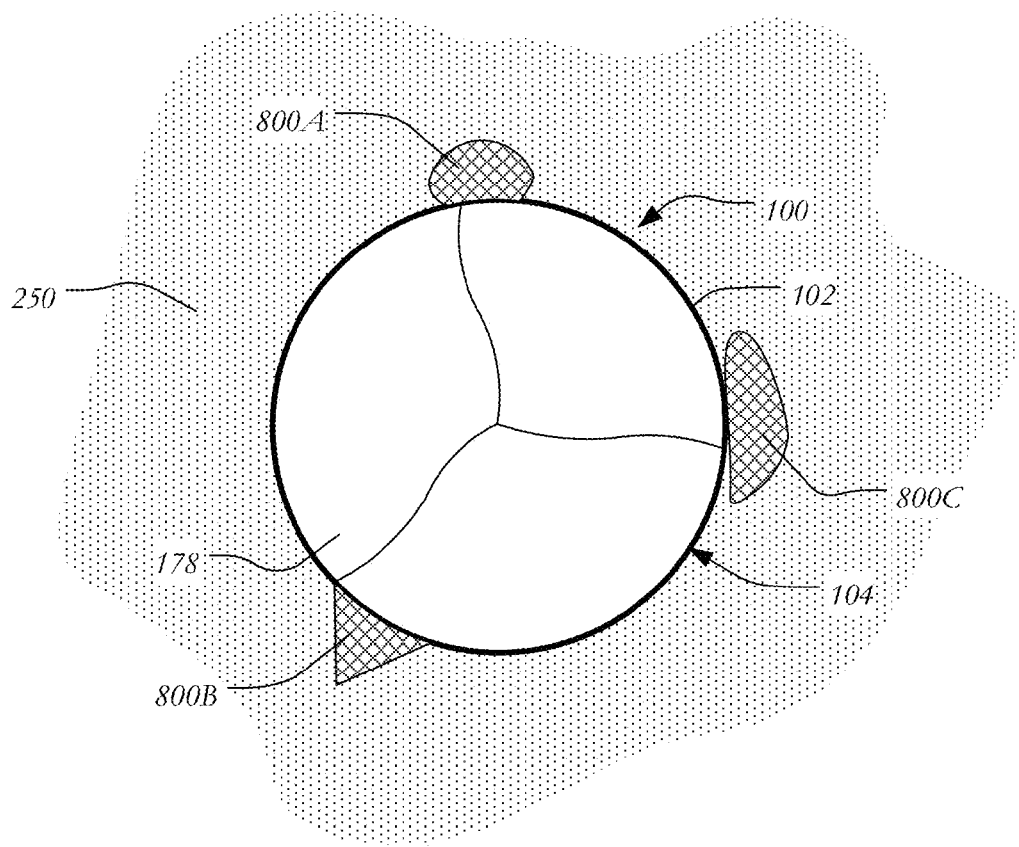
FIG. 9 is a highly schematic cross-sectional view showing a prosthetic heart valve disposed within a native valve annulus along with the conformable occluders of FIGS. 8A-C in their fully expanded states.

FIG. 9 is a highly schematic cross-sectional view showing conformable occluders 800A-C fully radially expanded to fill multiple gaps between native valve annulus 250 and heart valve 100. The material of conformable occluders 800A-C may be capable of promoting tissue growth between heart valve 100 and native valve annulus 250. For example, conformable occluders 800A-C may be treated with a biological or chemical agent to promote tissue growth on the conformable occluder, further sealing the heart valve within the native valve annulus. When conformable occluders 800A-C functioning properly, heart valve 100 will be adequately sealed within native valve annulus 250 so that blood flows through valve assembly 104 and leaflets 178, while limiting or at least reducing blood flow through any gaps formed between heart valve 100 and native valve annulus 250.

Figure 10:
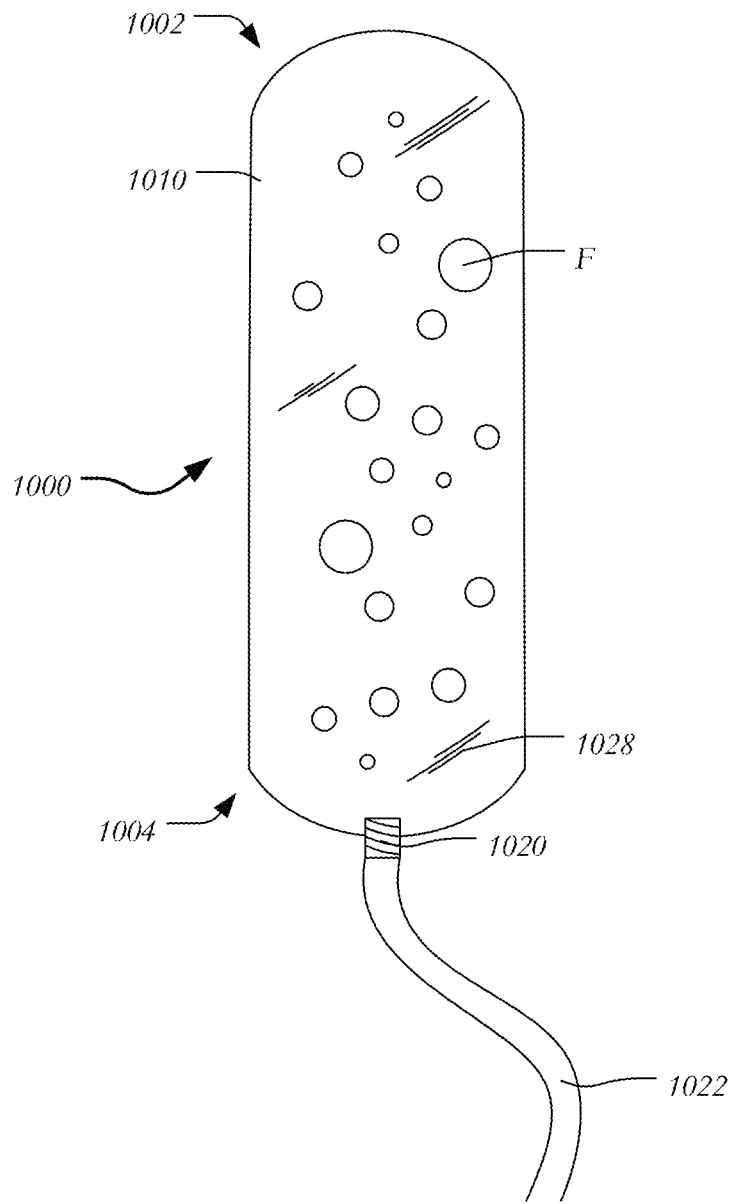
FIG. 10 is a side view illustrating the filling process of a conformable occluder.

As briefly indicated, occluders 800 may be supplied with a filler. FIG. 10 illustrates the process of filling conformable occluder 1000, which has a leading end 1002 and a trailing end 1004, and generally includes an elongated balloon-like body 1010 extending between leading end 1002 and trailing end 1004. Port 1020 at trailing end 1004 has been coupled to filling tube 1022 to allow hollow body 1010 to be at least partially filled with filler F, which may be a gas or a liquid, such as water or saline. Filler F may also be introduced to body 1010 either prior to or after delivery to a desired location and may include a suitable polymer a foam, sponge, collagen, polyester threads or polyester fabric, a hydrophilic material or other suitable material that may be compressed. If a liquid or gas is used, body 1010 may include an outer leak-proof coating 1028 or may include a tight weave of a braided material to encapsulate the filler material.

Figure 11:
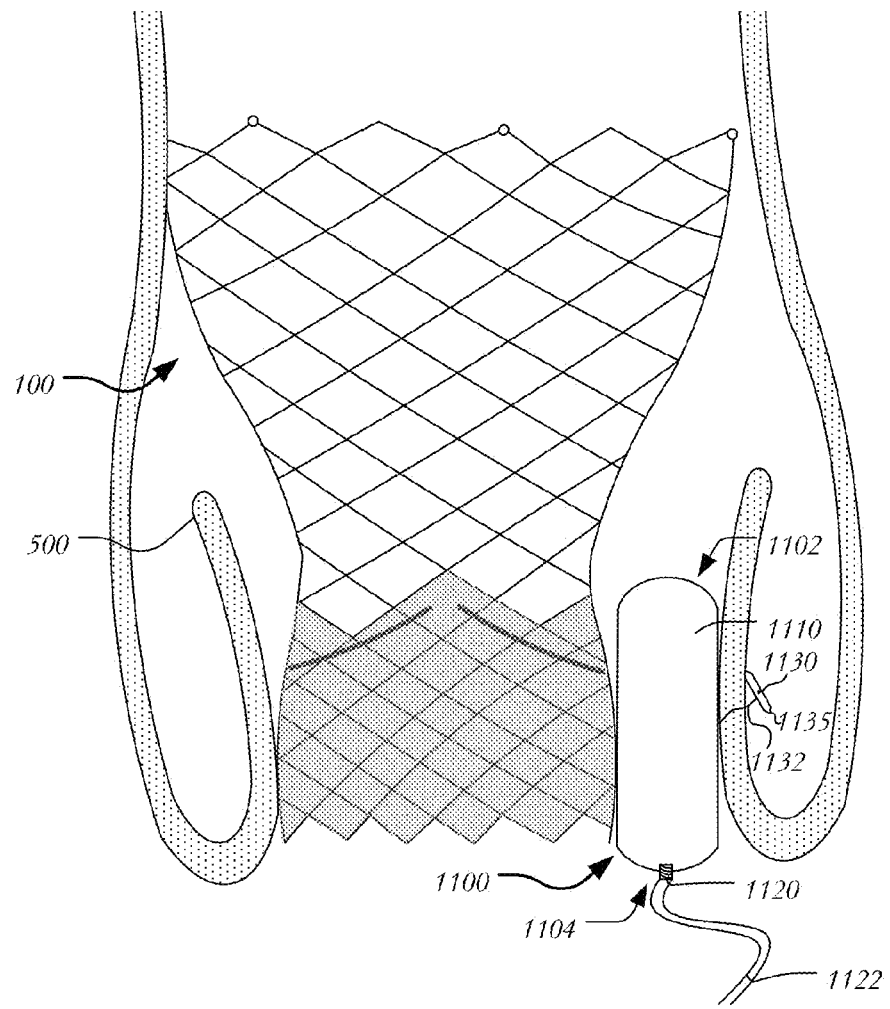
FIGS. 11-18 illustrate several techniques for fixing occluders in place between a heart valve and a native valve leaflet.

FIGS. 11-18 illustrate several techniques for fixing occluders in place between a heart valve and a native valve leaflet. Though these figures illustrate occluders being delivered transapically, it will be understood that transfemoral, transseptal, transaortic, transradial, transsubclavian and other approaches may also be used. In FIG. 11, occluder 1100 is disposed between heart valve 100 and native valve leaflet 500. Occluder 1100 extends between leading end 1102 and trailing end 1104 and includes body 1110 having port 1120 for filling body 1110 via filling tube 1122. Occluder 1100 further includes anchor 1130 attached to body 1110 via cord 1132. Anchor 1130 may include one or more sharp ends 1135 for piercing through native valve leaflets 500. Once anchor 1130 has passed through native valve leaflet 500, occluder 1100 is effectively affixed to native valve leaflet 500 and secured in place between heart valve 100 and native valve leaflet 500. In one variation of this embodiment, anchor 1130 may be configured to secure occluder 1100 to heart valve 100 by being fastened to select cells of stent 102.

Figure 12:
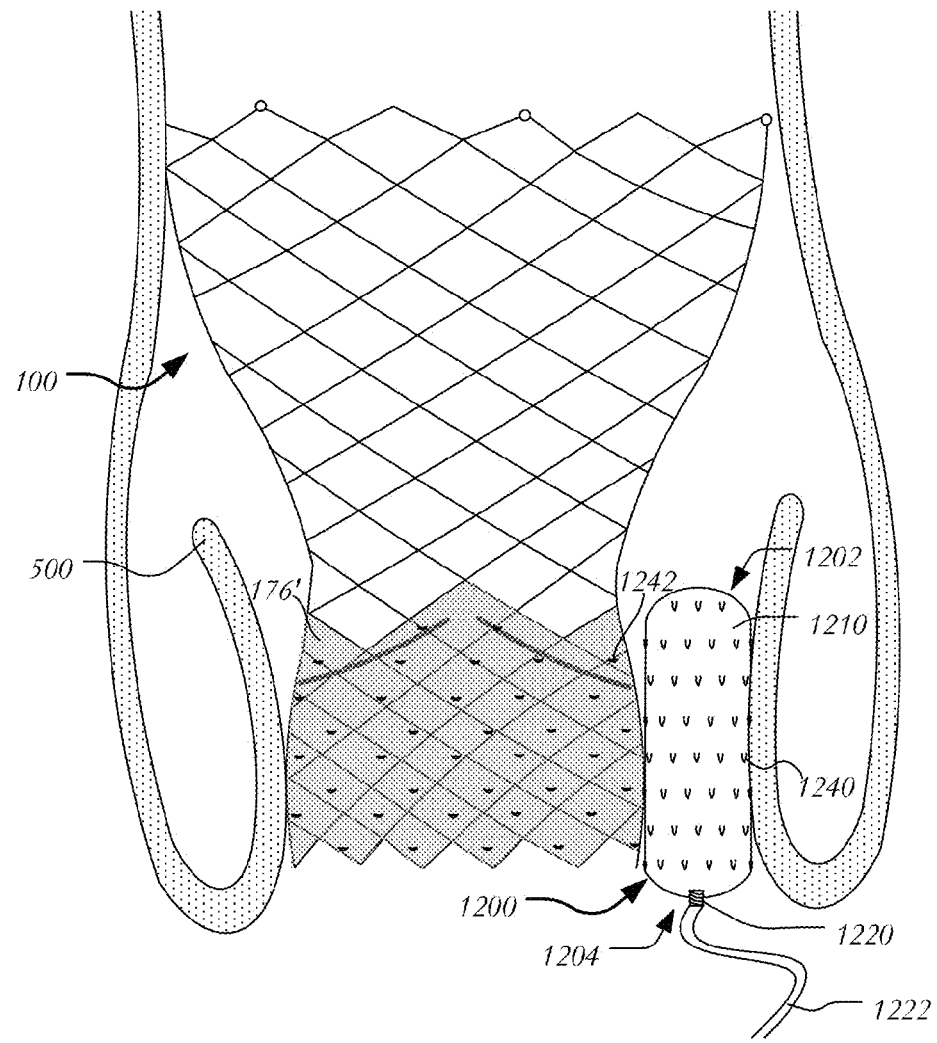

In a second embodiment, velcro-like elements secure the occluder in place between heart valve 100 and native valve leaflet 500 (FIG. 12). Occluder 1200 extends between leading end 1202 and trailing end 1204 and includes body 1210 having port 1220 for filling body 1210 via filling tube 1222. Occluder 1200 further includes a plurality of hooks 1240 on the surface of body 1210 configured and arranged to mate with perforations 1242 of porous cuff 176' of heart valve 100. Hooks 1240 may further be configured to grab onto native valve leaflet 500. As shown, hooks 1240 may be downwardly disposed (e.g., point toward trailing end 1204 of body 1210) and thus prevent occluder 1200 from migrating into the ventricle. Alternatively, hooks 1240 may be upwardly disposed to prevent occluder 1200 from being upwardly displaced into the aorta or a portion of hooks 1240 may be disposed in each orientation to secure the occluder and prevent movement in both directions.

Figure 13:
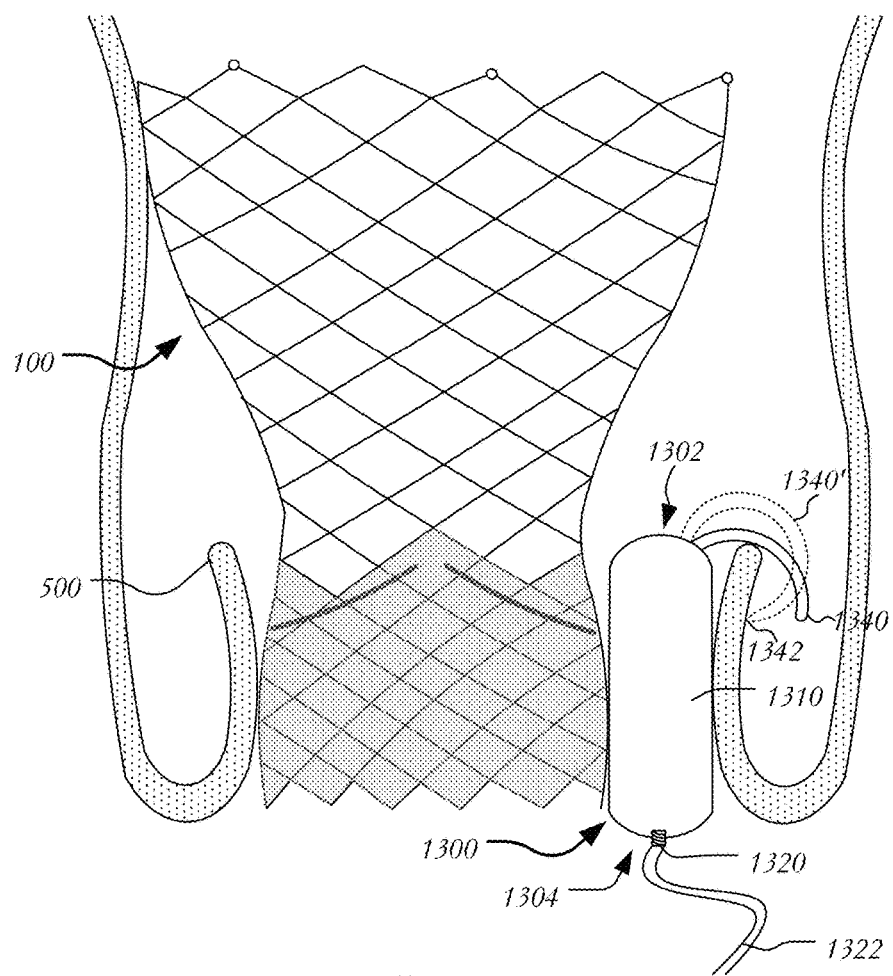

In a third embodiment, a clasp secures the occluder in place between heart valve 100 and native valve leaflet 500 (FIG. 13). Occluder 1300 extends between leading end 1302 and trailing end 1304 and includes body 1310 having port 1320 for filling body 1310 via filling tube 1322. Occluder 1300 further includes a curved clasp 1340 on the surface of body 1310 near leading end 1302 configured and arranged to cup over native valve leaflets 500. Clasp 1340 may be formed of a suitable metal or polymer. In one variation, shown in dashed lines, clasp 1340' is curved over native valve leaflets 500 and includes a sharp edge 1342 that pierces into native valve leaflet 500 to secure occluder 1300 in place. The fact that clasp 1340 curves over the free end of native valve leaflet 500 prevents occluder 1300 from migrating into the ventricle.

Figure 14:
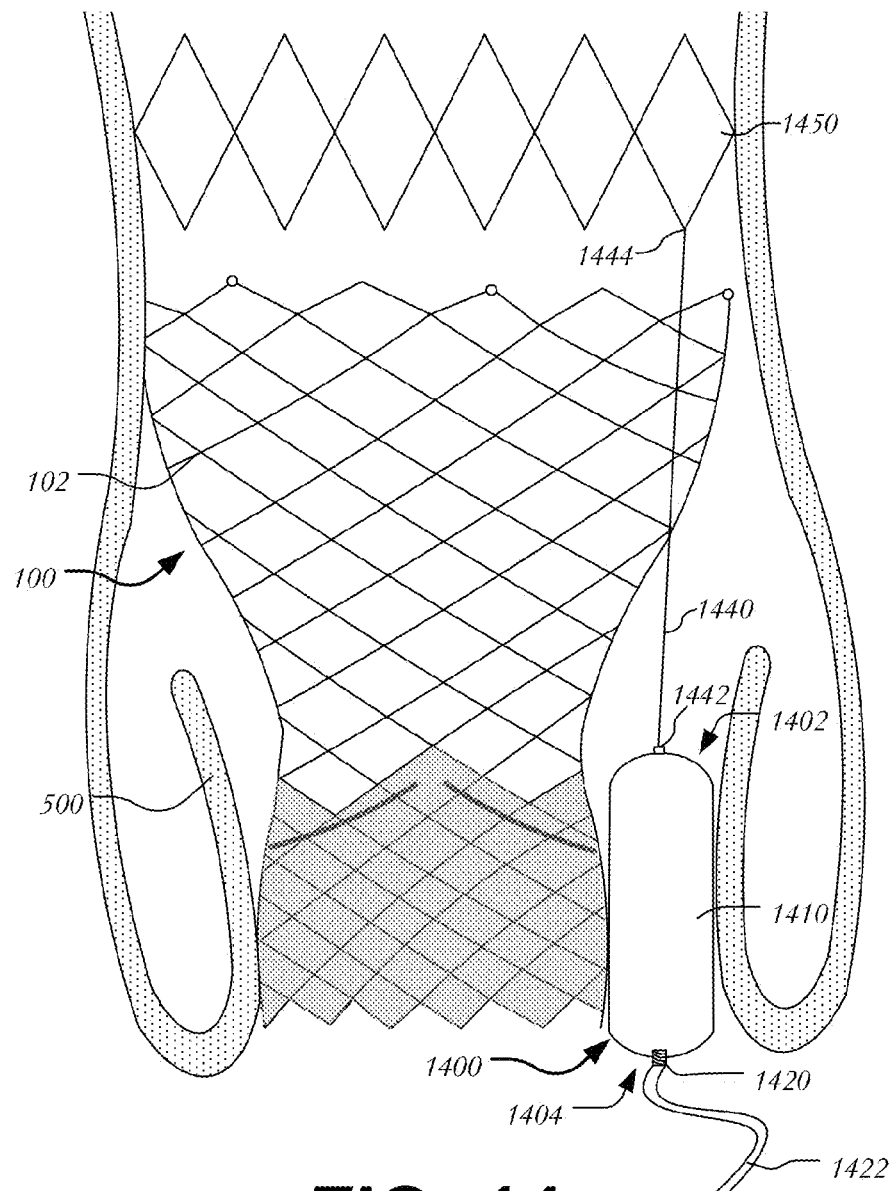

In a fourth embodiment, the occluder is secured between heart valve 100 and native valve leaflet 500 via an anchoring ring and a tether (FIG. 14). Occluder 1400 extends between leading end 1402 and trailing end 1404 and includes body 1410 having port 1420 for filling body 1410 via filling tube 1422. Occluder 1400 further includes tether 1440 having a first end 1442 attached to body 1410 near leading end 1402 and a second end 1444 attached to anchoring ring 1450. Tether 1440 may be formed of a suture, cord or any suitable biocompatible thread. Anchoring ring 1450 may be formed of a collapsible and expandable metal similar to that of stent 102 of heart valve 100 and dimensioned to be disposed above heart valve 100 (e.g., closer to the aorta than heart valve 100). By securing anchoring ring 1450 in place and securing occluder 1400 to the anchoring ring, occluder 1400 is prevented from migrating into a ventricle.

Figure 15:
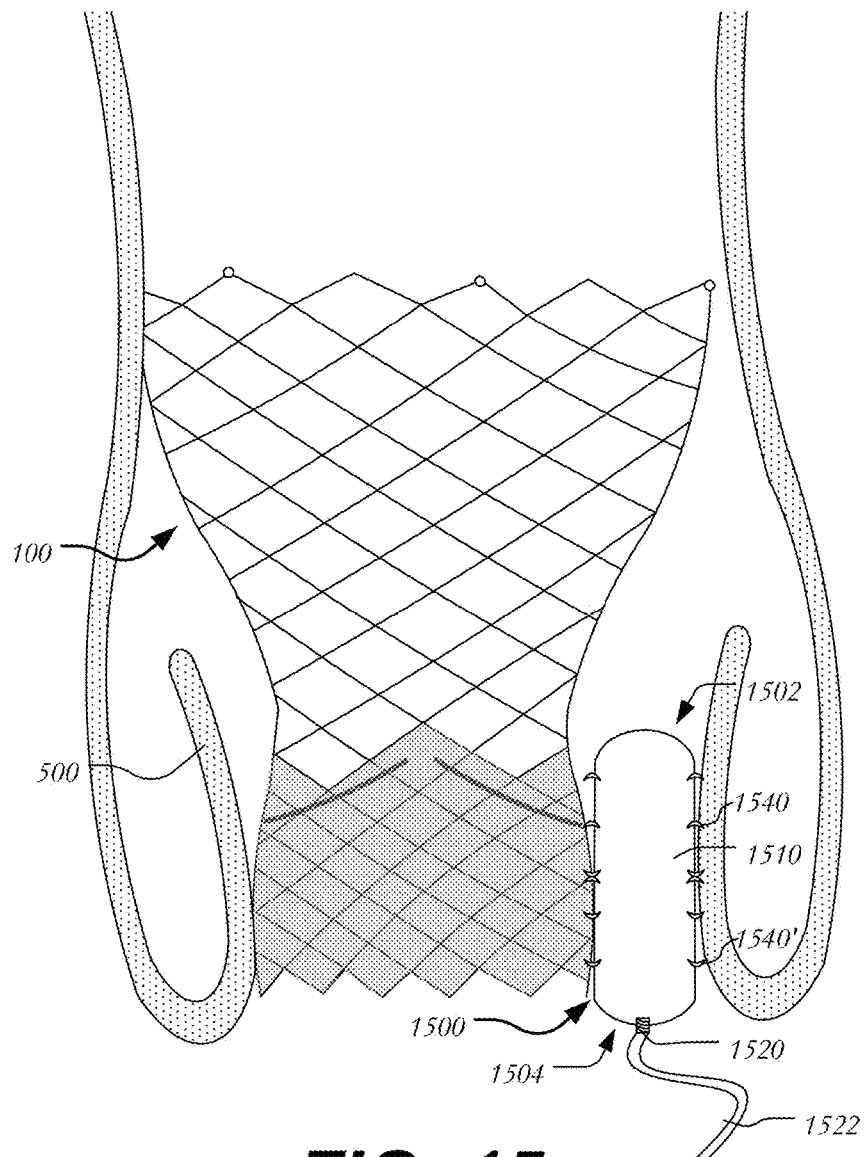

In a fifth embodiment, the occluder is secured between heart valve 100 and native valve leaflet 500 via barbs (FIG. 15). Occluder 1500 extends between leading end 1502 and trailing end 1504 and includes body 1510 having port 1520 for filling body 1510 via filling tube 1522. Occluder 1500 further includes a plurality of barbs 1540 on body 1510. Barbs 1540 may be circumferentially disposed about body 1510 and configured and arranged to couple body 1510 to heart valve 100 and to native valve leaflet 500. Barbs 1540 may be angled or shaped to prevent occluder 1500 from migrating toward the ventricle. Certain barbs 1540' may be oppositely angled or shaped to prevent occluder 1500 from being displaced toward the aorta.

Figure 16:
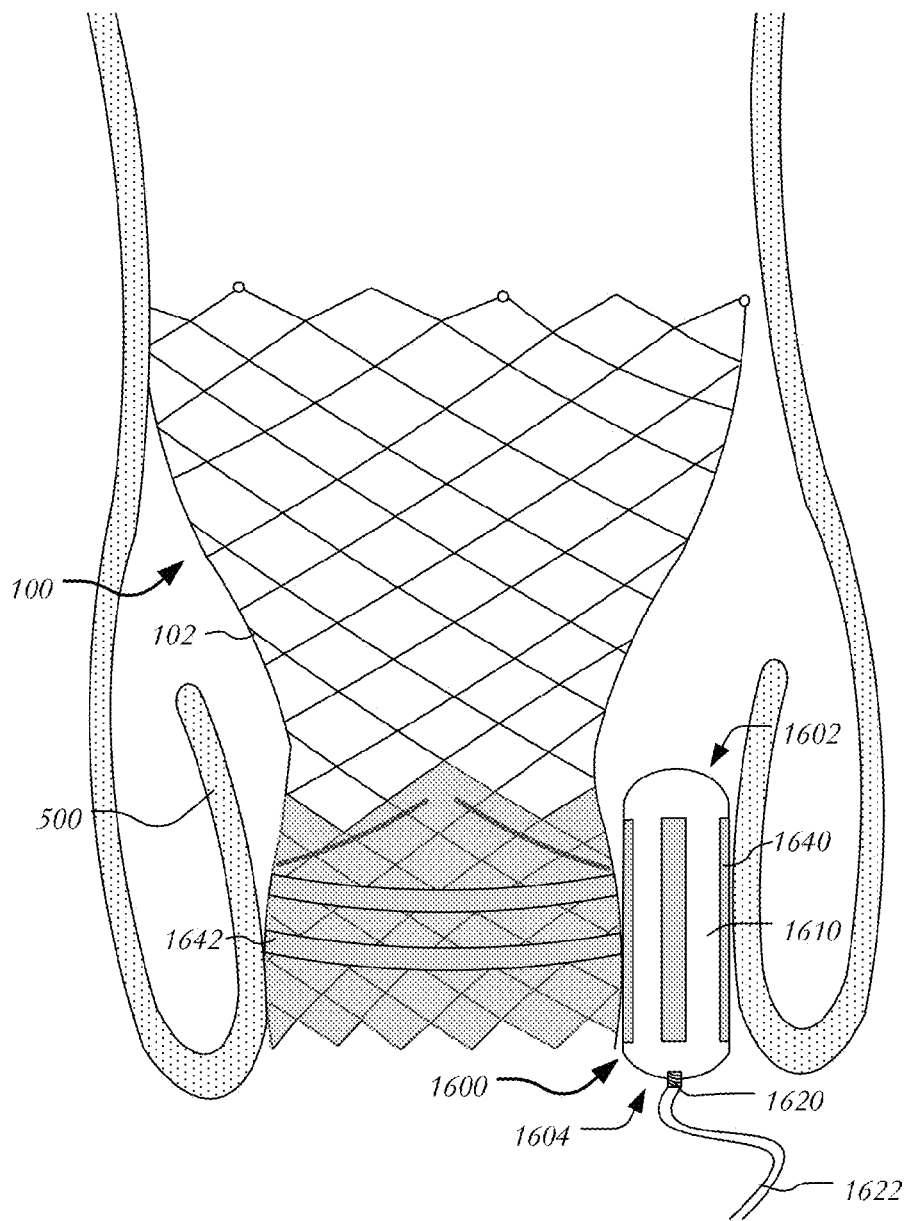

A sixth embodiment utilizes magnets to secure the occluder between heart valve 100 and native valve leaflet 500 (FIG. 16). Occluder 1600 extends between leading end

1602 and trailing end 1604 and includes body 1610 having port 1620 for filling body 1610 via filling tube 1622. Occluder 1600 includes a plurality of longitudinal magnetic strips 1640 circumferentially spaced about body 1610 and configured to couple to complementary magnetic strips 1650 attached to heart valve 100. Alternatively, stent 102 may be magnetized or made from a material capable of being magnetically coupled to strips 1640 of occluder 1600. It will be understood that in some variations, body 1610 and stent 102 may themselves be sufficiently magnetized so as to couple together without the need for intermediate elements.

Figure 17:
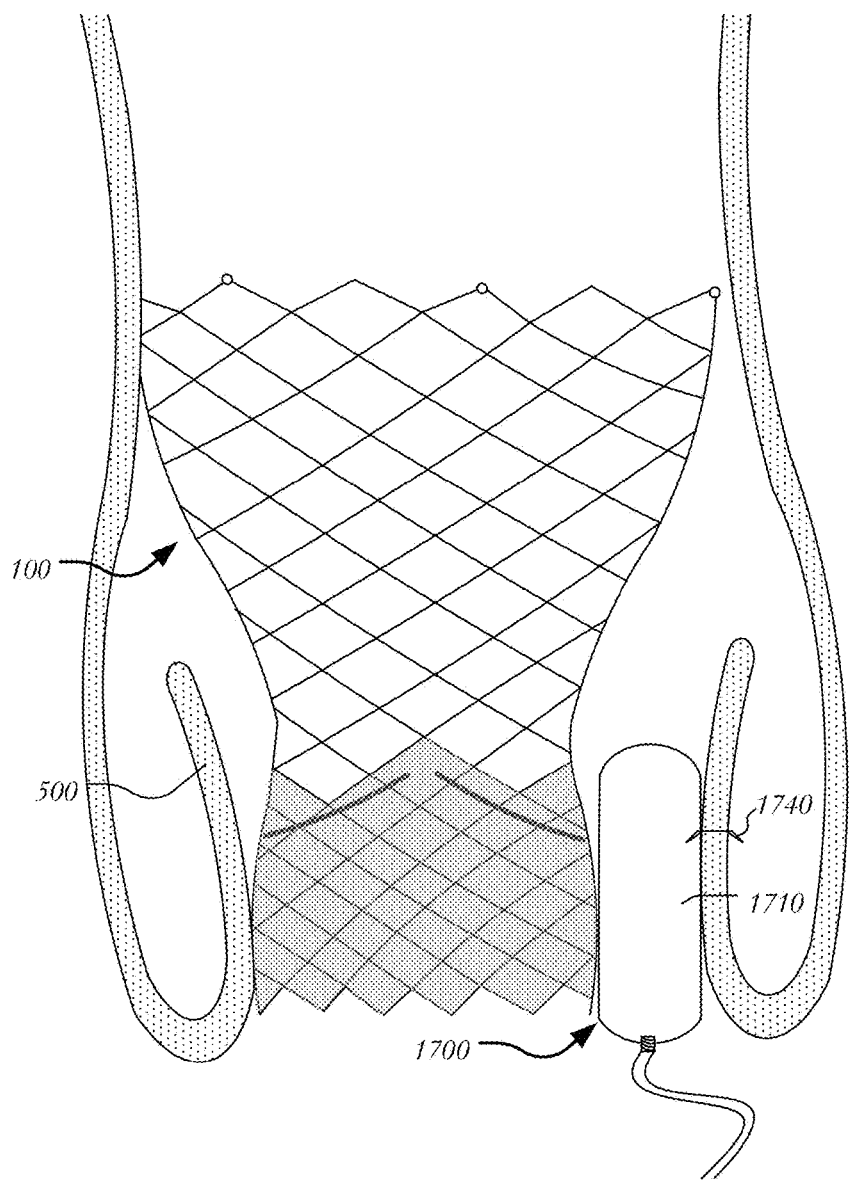

In a seventh embodiment, a staple may be used to couple body 1710 of occluder 1700 to heart valve 100 and/or to native valve leaflet 500 (FIG. 17). Staple 1740 may be formed of a metal or other suitable material. Staple 1740 may be separable from body 1710 and deployed after implantation of heart valve 100 and occluder 1700. It will be understood that multiple staples may be used around and/or along the periphery of body 1710.

Figure 18:
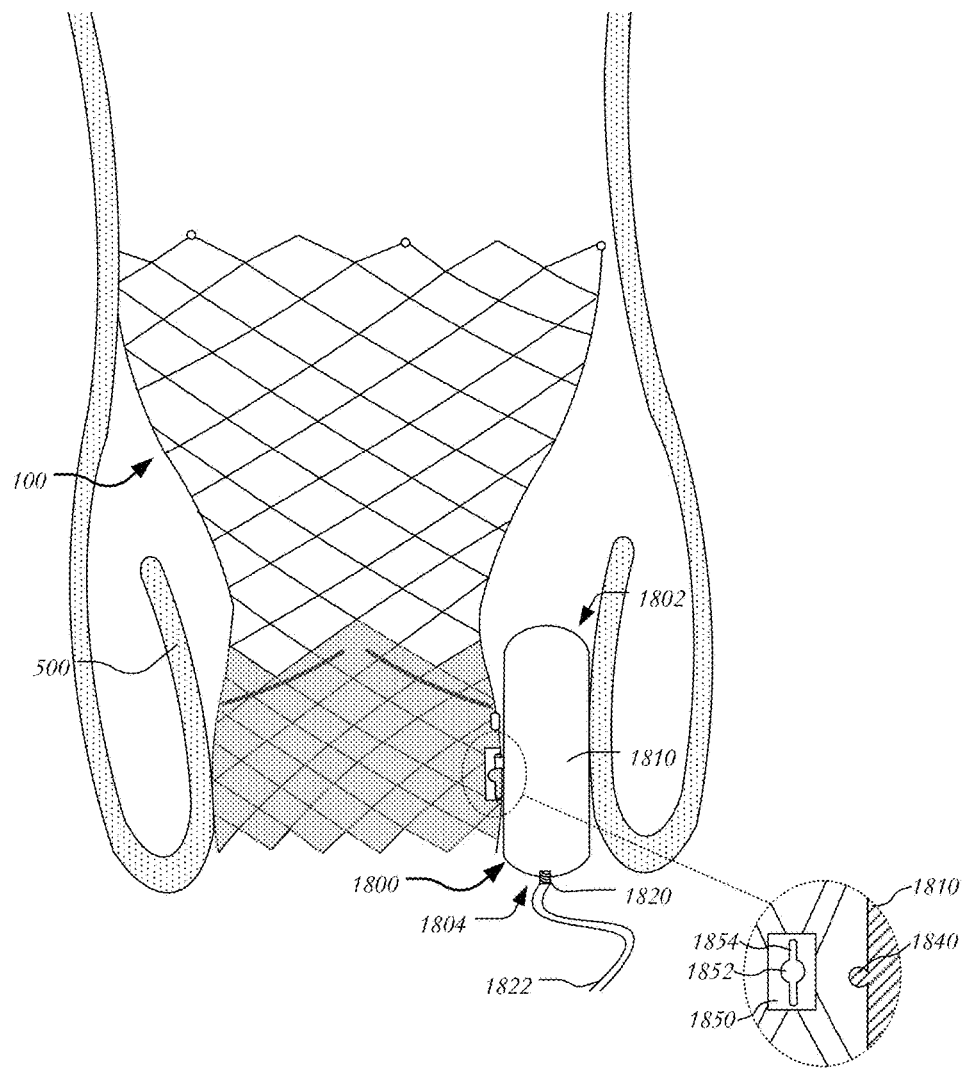

An eighth embodiment utilizes locking features to secure the occluder between heart valve 100 and native valve leaflet 500 (FIG. 18). Occluder 1800 extends between leading end 1802 and trailing end 1804 and includes body 1810 having port 1820 for filling body 1810 via filling tube 1822. Occluder 1800 includes a bit 1840 protruding from body 1810. In one example, bit 1840 is formed as a substantially spherical body, though it will be understood that one of ordinary skill in the art may utilize other shapes for bit 1840. Heart valve 100 may include receiver 1850 having a narrow vertical slot 1854 for locking bit 1840 in place. An enlarged opening 1852 is sized to receive bit 1840 and to guide bit 1840 into narrow slot 1854. Bit 1840 may be sized to pass through enlarged opening 1852 but not narrow slot 1854. In operation, bit 1840 is incapable of decoupling from receiver 1850 at the ends of narrow slot 1854. Thus, when occluder 1800 moves upward toward the aorta or downward toward the ventricle, occluder 1800 will remain secured to heart valve 100. It will be understood that modifications may be made to have the same effect. For example, various male and female components as known in the art may be used instead of bit 1840 and receiver 1850 to couple heart valve 100 and occluder 1800.

While the inventions herein have been described for use in connection with heart valve stents having a particular shape, the stent could have different shapes, such as a flared or conical annulus section, a less-bulbous aortic section, and the like, and a differently shaped transition section. Additionally, though the conformable occluders have been described in connection with expandable transcatheter aortic valve replacement, they may also be used in connection with surgical valves, sutureless valves and other devices in which it is desirable to create a seal between the periphery of the device and the adjacent body tissue. Additionally, though the deployment of the occluder has been described with fastener 320 deployed first, followed by body 310 and finally disk 330, it will be understood that, through a different delivery approach, such as, for example, a transapical route, disk 330 may be deployed first, followed by body 310 and then fastener 320. Radiopaque elements may be included on body 310, fastener 320, disk 330 or any portion of an occluder to aid in guiding and placement.

It will also be understood that while the preceding disclosure has illustrated the use of a single occluder to fill gaps to one side of a prosthetic heart valve, it will be understood that multiple occluders may be deployed around the perimeter of a heart valve. Such occluders may be delivered successively to each gap formed between the prosthetic heart valve and the native valve annulus. Where multiple occluders are used, they may be of different sizes to accommodate different size gaps. Conversely, multiple occluders may be delivered simultaneously using a large single outer sheath having two or more male components or other connectors. Additionally, multiple occluders may be simultaneously deployed by using multiple delivery systems each having a male component or other connector. Moreover, though the securing features have been described in one manner, it will be understood that where the occluders are delivered through a different approach, securing features may be moved from the leading end to the trailing end of the occluder and vice versa.

Moreover, although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

In some embodiments, an occluder device for occluding a gap between a medical device and adjacent body tissue includes a conformable body having a hollow interior, a leading end and a trailing end; and a port disposed at the trailing end of the body and in fluid communication with the interior of the body.

In some examples, the body may be an elongated balloon-like structure; and/or the body may be a triangular prism; and/or the body may be accordion-like and includes a plurality of bellows that expand and contract to change the shape of the body; and/or the medical device may be a prosthetic heart valve having a collapsible and expandable stent forming cells, and a valve assembly disposed in the stent for controlling the flow of blood through the stent and wherein the body is crescent-shaped and has a curvature that complements a curvature of the heart valve; and/or the occluder device may further include a source of in fluid communication with the port; and/or the occluder device may further include a source of polymeric filler in fluid communication with the port.

In some embodiments, an occluder device for occluding a gap between a medical device and adjacent body tissue includes a conformable body having a leading end and a trailing end; and a securing feature coupleable to the conformable body and at least one of the medical device and the adjacent body tissue.

In some examples, the securing feature may include an anchor and a cord for coupling the anchor to the body, the anchor being configured to couple to at least one of the medical device and the adjacent body tissue; and/or the anchor may have at least one sharp end for piercing the adjacent body tissue; and/or the securing feature may include a plurality of velcro-like hooks disposed on the body and the medical device includes a cuff having perforations coupleable to the plurality of hooks; and/or the securing feature may include a clasp coupled to the leading end of the body, the clasp being configured to cup over the adjacent body tissue; and/or the clasp may have a sharp end for piercing the adjacent body tissue and/or the securing feature may include a tether having a first end secured to the leading end of the body and a second end secured to an anchoring ring, the anchoring ring being spaced away from the medical device; and/or the securing feature may include a plurality of barbs disposed on the body; and/or the securing feature may include a first magnetic element on the occluder device and a second magnetic element on the medical device, the first magnetic element and the second magnetic element being configured to attract one another to secure the occluder device to the medical device; and/or the securing feature may include a staple for securing the body to the adjacent body tissue; and/or the securing feature may include a locking feature including a bit protruding from the body of the occluder device and a receiver coupled to the medical device and having an aperture sized to receive the bit; and/or the receiver may include a narrow slot with an enlarged opening therein, the bit being sized to pass through the enlarged opening but not the narrow slot.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A kit for repairing a damaged heart valve comprising:
   a prosthetic heart valve having a collapsible and expandable stent forming cells, the stent having a proximal end and a distal end, the prosthetic heart valve further including a valve assembly disposed in the stent for controlling the flow of blood through the stent; and
   an occluder disposed adjacent the proximal end of the stent and longitudinally extending in a lengthwise direction toward the distal end of the stent, the occluder configured to be disposed between the prosthetic heart valve and adjacent body tissue for occluding a gap between the prosthetic heart valve and the adjacent body tissue, the occluder having a first fastener for coupling to the stent and a second fastener for coupling to native heart tissue, the occluder having a delivery, pre-deployment configuration and a final, post-deployment configuration, the occluder in both the pre-deployment and post-deployment configurations including a conformable body having a fillable chamber, a leading end closer to the distal end of the stent and a trailing end closer to the proximal end of the stent, and a port disposed at the trailing end of the body and in fluid communication with the fillable chamber of the body, the body further having an outer coating configured to prevent leakage of a liquid or a gas.

2. The kit of claim 1, wherein the body is an elongated balloon-like structure.

3. The kit of claim 1, wherein the body is a triangular prism.

4. The kit of claim 1, wherein the body is accordion-like and includes a plurality of bellows that expand and contract to change the shape of the body.

5. The kit of claim 1, wherein the body is crescent-shaped and has a curvature that complements a curvature of the prosthetic heart valve.

6. The kit of claim 1, further comprising a source of gas in fluid communication with the port.

7. The kit of claim 1, further comprising a source of polymeric filler in fluid communication with the port.

8. The kit of claim 1, wherein the conformable body is configured to be spaced away from at least one native valve leaflet.

9. A kit for repairing a damaged heart valve comprising:
   a prosthetic heart valve having a collapsible and expandable stent forming cells, the stent having a proximal end and a distal end, the prosthetic heart valve further including a valve assembly disposed in the stent for controlling the flow of blood through the stent; and
   an occluder disposed adjacent the proximal end of the stent and longitudinally extending in a lengthwise direction toward the distal end of the stent, the occluder configured to be disposed between the prosthetic heart valve and adjacent body tissue for occluding a gap between the prosthetic heart valve and the adjacent body tissue, the occluder having a delivery, pre-deployment configuration and a final, post-deployment configuration, the occluder in both the pre-deployment and post-deployment configurations including an elongated balloon-like conformable body including a fillable chamber that is closed in the post-deployment configuration and having a leading end closer to distal end of the stent and a trailing end closer to the proximal end of the stent, and
   a securing feature having a first fastener disposed on the prosthetic heart valve and having a second fastener disposed on and projecting from a surface of the conformable body;
   the securing feature configured to couple the occluder to the stent.

10. The kit of claim 9, wherein the second fastener of the securing feature includes a plurality of hooks disposed on the body and the first fastener of the securing feature includes a cuff having a plurality of perforations, the plurality of hooks being coupleable to the perforations of the cuff.

11. The kit of claim 9, wherein the second fastener of the securing feature includes a first magnetic element disposed on the occluder and the first fastener of the securing feature includes a second magnetic element disposed on an annulus section of the prosthetic heart valve, the first magnetic element and the second magnetic element being configured to attract one another to secure the occluder to the annulus section of the prosthetic heart valve.

12. The kit of claim 9, wherein the second fastener of the securing feature includes a locking feature including a bit protruding from the body of the occluder and the first fastener of the securing feature includes a receiver coupled to an annulus section of the prosthetic heart valve and having an aperture sized to receive the bit.

13. The kit of claim 12, wherein the receiver includes a narrow slot with an enlarged opening therein, the bit being sized to pass through the enlarged opening but not the narrow slot.

* * * * *